US008194937B2

(12) United States Patent
Chen

(10) Patent No.: US 8,194,937 B2
(45) Date of Patent: Jun. 5, 2012

(54) METHOD FOR DYNAMIC PRIOR IMAGE CONSTRAINED IMAGE RECONSTRUCTION

(75) Inventor: Guang-Hong Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 901 days.

(21) Appl. No.: 12/253,400

(22) Filed: Oct. 17, 2008

(65) Prior Publication Data

US 2009/0161933 A1 Jun. 25, 2009

Related U.S. Application Data

(60) Provisional application No. 61/015,559, filed on Dec. 20, 2007, provisional application No. 61/020,847, filed on Jan. 14, 2008, provisional application No. 61/059,891, filed on Jun. 9, 2008.

(51) Int. Cl.
*G06K 9/00* (2006.01)

(52) U.S. Cl. ......... 382/118; 382/128; 382/131; 382/248

(58) Field of Classification Search .................. 382/118, 382/119, 128, 131, 132, 232, 248, 325; 378/4–20, 378/62, 98, 98.8, 210, 901
See application file for complete search history.

(56) References Cited

U.S. PATENT DOCUMENTS

| | | | |
|---|---|---|---|
| 6,841,998 B1 | 1/2005 | Griswold | |
| 7,289,049 B1 | 10/2007 | Fudge et al. | |
| 7,330,027 B2 | 2/2008 | Kozerke et al. | |
| 7,358,730 B2 | 4/2008 | Mistretta et al. | |
| 7,408,347 B2 | 8/2008 | Mistretta et al. | |
| 7,519,412 B2 | 4/2009 | Mistretta | |
| 7,545,901 B2 | 6/2009 | Mistretta | |
| 7,558,414 B2 | 7/2009 | Griswold | |
| 7,647,088 B2 | 1/2010 | Mistretta et al. | |
| 2006/0029279 A1 | 2/2006 | Donoho | |
| 2007/0009080 A1* | 1/2007 | Mistretta | ............................ 378/4 |
| 2007/0010731 A1 | 1/2007 | Mistretta | |
| 2007/0038073 A1 | 2/2007 | Mistretta | |
| 2007/0106149 A1 | 5/2007 | Mistretta | |
| 2007/0110290 A1* | 5/2007 | Chang et al. | .................. 382/128 |
| 2007/0156044 A1 | 7/2007 | Mistretta et al. | |

(Continued)

OTHER PUBLICATIONS

Chen et al "Prior image constrained compressed sensing "PICCS . . . : A method to accurately reconstruct dynamic CT images from highly undersampled projection data sets; Jan. 2008.*

(Continued)

*Primary Examiner* — Vikkram Bali
*Assistant Examiner* — Nancy Bitar
(74) *Attorney, Agent, or Firm* — Quarles & Brady LLP

(57) ABSTRACT

A method for reconstructing a high quality image from undersampled image data is provided. The image reconstruction method is applicable to a number of different imaging modalities. Specifically, the present invention provides an image reconstruction method that incorporates an appropriate prior image into the image reconstruction process. Thus, one aspect of the present invention is to provide an image reconstruction method that requires less number of data samples to reconstruct an accurate reconstruction of a desired image than previous methods, such as, compressed sensing. Another aspect of the invention is to provide an image reconstruction method that produces a time series of desired images indicative of a higher temporal resolution than is ordinarily achievable with the imaging system. For example, cardiac phase images can be produced with high temporal resolution (e.g., 20 milliseconds) using a CT imaging system with a slow gantry rotation speed.

20 Claims, 19 Drawing Sheets

U.S. PATENT DOCUMENTS

| | | | |
|---|---|---|---|
| 2007/0156045 | A1* | 7/2007 | Mistretta et al. ............. 600/410 |
| 2007/0167707 | A1 | 7/2007 | Mistretta et al. |
| 2007/0167728 | A1 | 7/2007 | Mistretta et al. |
| 2007/0167729 | A1 | 7/2007 | Mistretta et al. |
| 2008/0107319 | A1* | 5/2008 | Chang et al. ................. 382/131 |
| 2008/0199063 | A1 | 8/2008 | O'Halloran et al. |
| 2008/0219535 | A1* | 9/2008 | Mistretta et al. ............. 382/131 |
| 2008/0292167 | A1* | 11/2008 | Todd et al. ................... 382/131 |
| 2008/0304727 | A1* | 12/2008 | Doyle ........................... 382/131 |
| 2009/0076369 | A1 | 3/2009 | Mistretta |
| 2009/0092303 | A1* | 4/2009 | Griswold et al. ............. 382/131 |
| 2009/0129651 | A1 | 5/2009 | Zagzebski et al. |
| 2011/0044546 | A1* | 2/2011 | Pan et al. ..................... 382/195 |

OTHER PUBLICATIONS

Kim et al (An efficient Method for compressed Sensing )Stanford,CA Sep. 2007.*

Song Jiayu et al: Sparseness prior based iterative image reconstruction for retrospectively gated cardiac micro-CT ; Oct. 26, 2007.*

Fessler, et al., "Iterative Image Reconstruction in MRI With Separate Magnitude and Phase Regularization," IEEE International Symposium on Biomedical Imaging: Nano to Macro, 2004; 1:209-212.

Lustig, et al., "Rapid MR Imaging with 'Compressed Sensing' and Randomly Under-Sampled 3DFT Trajectories", Proc. Intl. Soc. Mag. Reson. Med. 14 (2006), p. 695.

Mistretta, et al., "Highly Constrained Backprojection for Time-Resolved MRI", Magn Reson Med, 2006, 55(1):30-40.

Donoho, "Compressed Sensing", Sep. 14, 2004, pp. 1-34.

Schmidt, "Least Squares Optimization with L1-Norm Regularization", Dec. 2005, pp. 1-12.

O'Halloran, et al., "Iterative Projection Reconstruction of Time-Resolved Images Using Highly-Constrained Back-Projection (HYPR)", Magn Reson Med, 2008, 59:132-139 (published online Dec. 3, 2007).

Michael Lustig, Student Member, IEEE; Compressed Sensing MRI; 18 pages; 2007.

Emmanuel J Cades et al; Robust Uncertainty Principles: Exact Signal Reconstruction From Highly Incomplete Frequency Information; IEEE Transactions on Information Theory, vol. 22, No. 2, Feb. 2006; 489-509.

David L Donoho, member IEEE; Compressed Sensing; IEEE Transactions on Information Theory, vol. 52, No. 4, Apr. 2006; 1289-1306.

Jiayu Song et al; Sparseness Prior Based Iterative Image Reconstruction for Retrospectively Gated Cardiac Micro-CT; Med. Phys. 34(11), Nov. 2007; pp. 4476-4483.

M. Lustig, et al., "Sparse MRI: The application of compressed sensing for rapid MR imaging" Magnetic Resonance in Medicine 58(6)1182-1195 (2007).

* cited by examiner

METHOD FOR DYNAMIC PRIOR IMAGE CONSTRAINED IMAGE RECONSTRUCTION

CROSS-REFERENCE TO RELATED APPLICATIONS

This application claims the benefit of U.S. Provisional Patent Application Ser. No. 61/015,559 filed on Dec. 20, 2007 and entitled "Method for Image Reconstruction Using Prior Image Constrained Compressed Sensing"; U.S. Provisional Patent Application Ser. No. 61/020,847 filed on Jan. 14, 2008 and entitled "Method for Image Reconstruction Using Prior Image Constrained Compressed Sensing"; and U.S. Provisional Patent Application Ser. No. 61/059,891 filed on Jun. 9, 2008 and entitled "Method for Image Reconstruction Using Prior Image Constrained Compressed Sensing".

STATEMENT REGARDING FEDERALLY SPONSORED RESEARCH

This invention was made with United States Government support awarded by the following agency: National Institutes of Health, NIH EB005712 and NIH EB007021. The United States Government has certain rights in this invention.

BACKGROUND OF THE INVENTION

The field of the invention is medical imaging and particularly, methods for reconstructing images from acquired image data.

In a computed tomography system, an x-ray source projects a fan-shaped beam which is collimated to lie within an x-y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile," or "attenuation profile" or "projection."

The source and detector array in a conventional CT system are rotated on a gantry within the imaging plane and around the object so that the angle at which the x-ray beam intersects the object constantly changes. The transmission profile from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This image reconstruction process converts the attenuation measurements acquired during a scan into integers called "CT numbers" or "Hounsfield units", which are used to control the brightness of a corresponding pixel on a display.

The filtered backprojection image reconstruction method is the most common technique used to reconstruct CT images from acquired transmission profiles. As shown in FIG. 1 each acquired x-ray transmission profile 100 is backprojected onto the field of view (FOV) 102 by projecting each ray sum 104 in the profile 100 through the FOV 102 along the same ray path that produced the ray sum 104 as indicated by arrows 106. In projecting each ray sum 104 in the FOV 102 we have no a priori knowledge of the subject and the assumption is made that the x-ray attenuation in the FOV 102 is homogeneous and that the ray sum should be distributed equally in each pixel through which the ray path passes. For example, a ray path 108 is illustrated in FIG. 1 for a single ray sum 104 in one transmission profile 100 and it passes through N pixels in the FOV 102. The attenuation value, P, of this ray sum 104 is divided up equally between these N pixels:

$$\mu_n = \frac{(P \times 1)}{N}$$

where $\mu_n$ is the attenuation value distributed to the $n^{th}$ pixel in a ray path having N pixels.

Clearly, the assumption that attenuation in the FOV 102 is homogeneous is not correct. However, as is well known in the art, if certain corrections are made to each transmission profile 100 and a sufficient number of profiles are acquired at a corresponding number of projection angles, the errors caused by this faulty assumption are minimized and image artifacts are suppressed. In a typical filtered backprojection method of image reconstruction, anywhere from 400 to 1000 views are typically required to adequately suppress image artifacts in a 2D CT image.

Another issue with x-ray CT is the x-ray dose to which the subject is exposed during the scan. To obtain a higher resolution and artifact free image it is necessary to obtain many views at a high enough x-ray beam intensity to reconstruct an image at the desired signal-to-noise ratio (SNR). The dose level may be reduced by decreasing the beam strength or reducing the number of acquired views, but either step also reduces the SNR of the reconstructed image.

In general, cardiac CT imaging is a particularly demanding task. For example, sub-millimeter isotropic spatial resolution is necessary in order to visualize the small branches of the coronary arteries. Initially, computed tomography of the heart was performed by electron beam CT (EBCT) without contrast media to assess coronary calcifications. The lack of moving parts enables EBCT to achieve scan times of 50 milliseconds or less. While EBCT acquisition provides high temporal resolution, it suffers from low spatial resolution, for example, 1.2 millimeter in-plane resolution with 3 millimeter slice thickness. In recent years, tremendous improvements have been made in conventional rotating-gantry CT. In the state-of-the-art 64-slice, or 320-slice, multi-row detector CT (MDCT), 0.6×0.6×0.6 mm³ isotropic spatial resolution is achievable. Moreover, a state-of-the-art CT gantry may revolve at 0.27 seconds per revolution for single source-detector system, which allows for cardiac imaging with 150 millisecond temporal resolution.

Magnetic resonance imaging (MRI) uses the nuclear magnetic resonance (NMR) phenomenon to produce images. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_{xy}$. A signal is emitted by the excited spins, and after the excitation signal $B_1$ is terminated, this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. Each measurement is referred to in the art as a "view" and the number of views determines the quality of the image. The resulting set of received NMR signals, or views, or k-space samples, are digitized and processed to reconstruct the image using one of many well known reconstruction techniques. The total scan time is determined in part by the length of each measurement cycle, or "pulse sequence", and in part by the number of measurement cycles, or views, that are acquired for an image. There are many clinical applications where total scan time for an image of prescribed resolution and SNR is a premium, and as a result, many improvements have been made with this objective in mind.

Projection reconstruction methods have been known since the inception of magnetic resonance imaging and this method is again being used as disclosed in U.S. Pat. No. 6,487,435. Rather than sampling k-space in a rectilinear, or Cartesian, scan pattern as is done in Fourier imaging and shown in FIG. 2A, projection reconstruction methods sample k-space with a series of views that sample radial lines extending outward from the center of k-space as shown in FIG. 2B. The number of views needed to sample k-space determines the length of the scan and if an insufficient number of views are acquired, streak artifacts are produced in the reconstructed image. The technique disclosed in U.S. Pat. No. 6,487,435 reduces such streaking by acquiring successive undersampled images with interleaved views and sharing peripheral k-space data between successive image frames.

Two example methods used to reconstruct images from an acquired set of projection views are described, for example, in U.S. Pat. No. 6,710,686. In MRI the most common method is to regrid the k-space samples from their locations on the radial sampling trajectories to a Cartesian grid. The image is then reconstructed by performing a 2D or 3D Fourier transformation of the regridded k-space samples. The second method for reconstructing an MR image is to transform the radial k-space projection views to Radon space by first Fourier transforming each projection view. An image is reconstructed from these signal projections by filtering and back-projecting them into the field of view (FOV). As is well known in the art, if the acquired signal projections are insufficient in number to satisfy the Nyquist sampling theorem, streak artifacts are produced in the reconstructed image.

Depending on the technique used, many MR scans currently used to produce medical images require many minutes to acquire the necessary data. The reduction of this scan time is an important consideration, since reduced scan time increases patient throughout, improves patient comfort, and improves image quality by reducing motion artifacts. Many different strategies have been developed to shorten the scan time.

One such strategy is referred to generally as "parallel imaging". Parallel imaging techniques use spatial information from arrays of RF receiver coils to substitute for the encoding that would otherwise have to be obtained in a sequential fashion using RF pulses and field gradients (such as phase and frequency encoding). Each of the spatially independent receiver coils of the array carries certain spatial information and has a different sensitivity profile. This information is utilized in order to achieve a complete location encoding of the received MR signals by a combination of the simultaneously acquired data received from the separate coils. Specifically, parallel imaging techniques undersample k-space by reducing the number of acquired phase-encoded k-space sampling lines while keeping the maximal extent covered in k-space fixed. The combination of the separate MR signals produced by the separate receiver coils enables a reduction of the acquisition time required for an image (in comparison to conventional k-space data acquisition) by a factor that in the most favorable case equals the number of the receiver coils. Thus the use of multiple receiver coils acts to multiply imaging speed, without increasing gradient switching rates or RF power.

Two categories of such parallel imaging techniques that have been developed and applied to in vivo imaging are SENSE (SENSitivity Encoding) and SMASH (SiMultaneous Acquisition of Spatial Harmonics). With SENSE, the undersampled k-space data is first Fourier transformed to produce an aliased image from each coil, and then the aliased image signals are unfolded by a linear transformation of the superimposed pixel values. With SMASH, the omitted k-space lines are filled in or reconstructed prior to Fourier transformation, by constructing a weighted combination of neighboring lines acquired by the different receiver coils. SMASH requires that the spatial sensitivity of the coils be determined, and one way to do so is by "autocalibration" that entails the use of variable density k-space sampling.

The data acquisition methods are significantly different in the above exemplary imaging modalities. Namely, k-space is sampled to measure Fourier coefficients in MR data acquisitions while line integrals are measured in x-ray CT data acquisitions. Despite this, the challenge in image reconstruction for both modalities is common: reconstructing a quality image from an undersampled data set.

According to standard image reconstruction theories, in order to reconstruct an image without aliasing artifacts, the sampling rate employed to acquire image data must satisfy the so-called Nyquist criterion, which is set forth in the Nyquist-Shannon sampling theorem. Moreover, in standard image reconstruction theories, no specific prior information about the image is needed. On the other hand, when some prior information about the desired image is available and appropriately incorporated into the image reconstruction procedure, an image can be accurately reconstructed even if the Nyquist criterion is violated. For example, if one knows a desired image is circularly symmetric and spatially uniform, only one view of parallel-beam projections (i.e., one projection view) is needed to accurately reconstruct the linear attenuation coefficient of the object. As another example, if one knows that a desired image consists of only a single point, then only two orthogonal projections that intersect at said point are needed to accurately reconstruct the image point. Thus, if prior information is known about the desired image, such as if the desired image is a set of sparsely distributed points, it can be reconstructed from a set of data that was acquired in a manner that does not satisfy the Nyquist criterion. Put more generally, knowledge about the sparsity of the desired image can be employed to relax the Nyquist criterion; however, it is a highly nontrivial task to generalize these arguments to formulate a rigorous image reconstruction theory.

The Nyquist criterion serves as one of the paramount foundations of the field of information science. However, it also plays a pivotal role in modern medical imaging modalities such as magnetic resonance imaging (MRI) and x-ray computed tomography (CT). When the number of data samples acquired by an imaging system is less than the requirement imposed by the Nyquist criterion, artifacts appear in the reconstructed images. In general, such image artifacts include aliasing and streaking artifacts. In practice, the Nyquist criterion is often violated, whether intentionally or through unavoidable circumstances. For example, in order to shorten the data acquisition time in a time-resolved MR angiography study, undersampled projection reconstruction, or radial, acquisition methods are often intentionally introduced.

Recently, a new mathematical framework for image reconstruction termed "compressed sensing" (CS) was formulated. In compressed sensing, only a small set of linear projections of a sparse image are required to reconstruct a quality image. The theory of CS is described in E. Candès, J. Romberg, and T. Tao, "Robust uncertainty principles: Exact signal reconstruction from highly incomplete frequency information," *IEEE Transactions on Information Theory* 2006; 52:489-509, and D. Donoho, "Compressed sensing," *IEEE Transactions on Information Theory* 2006; 52:1289-1306, and is disclosed, for example, in U.S. patent application Ser. No. 11/199,675.

Although the mathematical framework of CS is elegant, the applicability of the reconstruction method to the field of medical imaging critically relies on the medical images being sparse. Unfortunately, a medical image is often not sparse in the standard pixel representation. Despite this, mathematical transforms can be applied to a single image in order to sparsify the image. Such transforms are thus referred to as "sparsifying transforms". More specifically, given a sparsifying transform, $\Psi$, CS image reconstruction is implemented by minimizing the following objective function:

$$\|\Psi I\|_1,$$

such that, $$AI=Y.$$

In the above objective function, I is a vector that represents the desired image, Y is a vector that represents the data acquired by the imaging system, A is a system matrix that describes the measurements, and $$\|x\|_1 = \sum_{i=1}^{N} |x_i|,$$

is the so-called $L_1$-norm of an N-dimensional vector, x. Namely, the CS image reconstruction determines an image that minimizes the $L_1$-norm of the sparsified image among all images that are consistent with the physical measurements, AI=Y.

The basic ideas in the compressed sensing image reconstruction theory can be summarized as follows. Instead of directly reconstructing a desired image in pixel representation, a sparsified version of the desired image is reconstructed. In the sparsified image, substantially fewer image pixels have significant image values; thus, it is possible to reconstruct the sparsified image from an undersampled data set. After the sparsified desired image is reconstructed, an "inverse sparsifying transform" is used to transform the sparsified image back to the desired image. In practice, there is no need to have an explicit form for the "inverse" sparsifying transform. In fact, only the sparsifying transform is needed in image reconstruction.

SUMMARY OF THE INVENTION

The present invention provides an image reconstruction method applicable to a number of different imaging modalities including x-ray computed tomography (CT), x-ray C-arm imaging, magnetic resonance imaging (MRI), positron emission tomography (PET), and single photon emission computed tomography (SPECT). More specifically, the present invention provides an image reconstruction method that combines the merits of accurate reconstruction with a gain in signal-to-noise ratio (SNR) by incorporating an appropriate prior image of the subject into the image reconstruction process. In addition to the increased SNR, the method of the present invention provides an increase in temporal resolution. Moreover, for a given desired image and a given number of projections, the method of the present invention provides accurate image reconstruction where previous image reconstruction methods, such as compressed sensing (CS) fail.

One aspect of the present invention provides a method for producing a time series of images indicative of a higher temporal resolution than the temporal resolution at which the corresponding image data was acquired. For example, the present invention provides a method for high temporal resolution cardiac imaging. For cardiac CT, a slow gantry rotation data acquisition is employed. More specifically, high temporal resolution is achievable that significantly improves the diagnostic accuracy of coronary CT angiography and measurement of cardiac function. Moreover, by using a slow gantry rotation during a single breath-hold, problems with view angle synchronization are significantly reduced. Increased temporal resolution is also achievable in MR imaging applications.

Another aspect of the present invention provides a fundamentally different way to increase temporal resolution for a conventional multi-detector CT (MDCT) scanner with a fast gantry rotation data acquisition system. More specifically, a gating window, such as a cardiac gating window, for a conventional filtered backprojection image reconstruction is divided into several subwindows, or "time windows". The present invention provides a way to reconstruct images using the data from each subwindow. This method of temporal resolution improvement is also achievable for slow gantry rotation CT imaging and MR imaging applications.

Another aspect of the present invention provides a fundamentally different form of segmented acquisition, where individual projections are segmented into to different cardiac phases, without the need to synchronize the gantry angle, or other data acquisitions, with the appropriate cardiac phase. In this way, excellent image quality can be achieved with the benefits of improved temporal resolution of segmented acquisitions. For example, in conventional multi-detector CT (MDCT), an irregular heart beat causes data gaps and overlap between different sectors. However, when practicing the present invention, an irregular heart beat only leads to a non-uniform distribution of the highly undersampled data set for each cardiac phase. This is true without dependence on the particular imaging modality utilized. This non-uniformity has very little effect on the images reconstructed in accordance with the present invention.

Yet another aspect of the present invention provides an accurate image reconstruction in cardiac imaging without a constraint on the patient's heart rate. In general, the higher a patient's heart rate, the more acquired projections available for each cardiac phase. Thus, improved image quality is achievable using the image reconstruction method of the present invention. More notably, an immediate clinical significance is that beta blockers are not required to be prescribed to the patient practicing the method of the present invention.

Yet another aspect of the present invention provides that the same imaging system utilized during catheter-based interventional procedures can be employed to produce a time-resolved four-dimensional cardiac "roadmap". This alleviates the need for tedious 3D-to-2D image registration during interventional procedures. This will be advantageous for hospitals in terms of imaging system space and resource allocation, in addition to more efficient patient throughput from a definitive diagnosis to a successful treatment.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
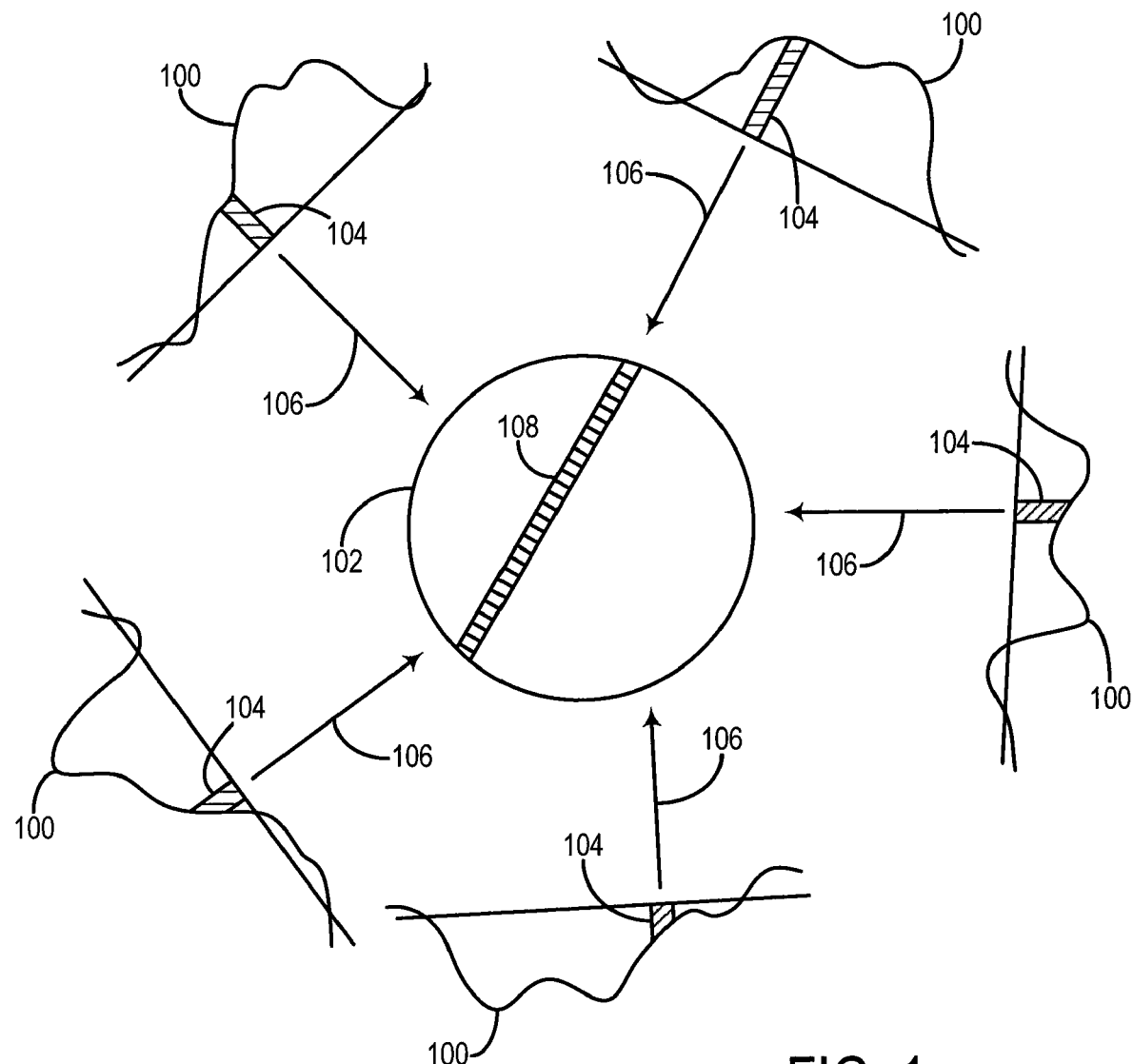
FIG. 1 is a pictorial representation of a conventional backprojection step in an image reconstruction process.
Figure 2A:
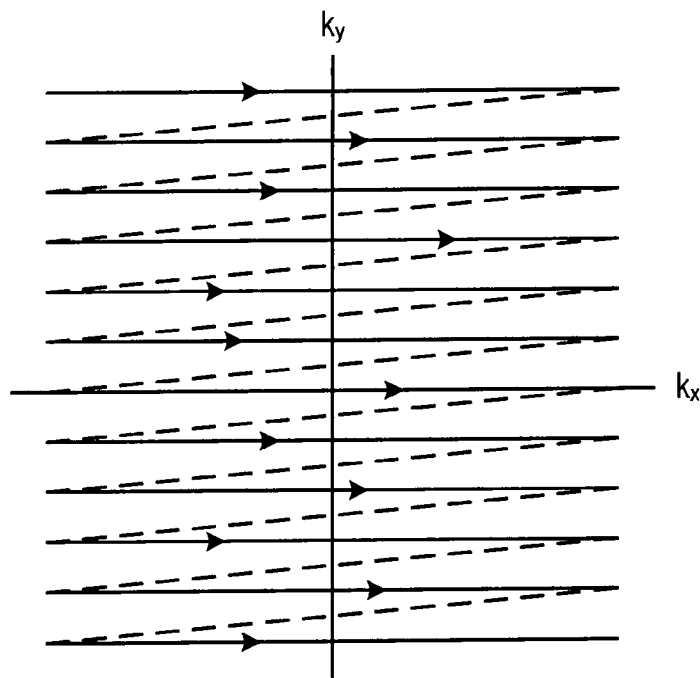
FIG. 2A is a graphic illustration of the manner in which k-space is sampled during a typical Fourier, or spin-warp, image acquisition using an MRI system.
Figure 2B:
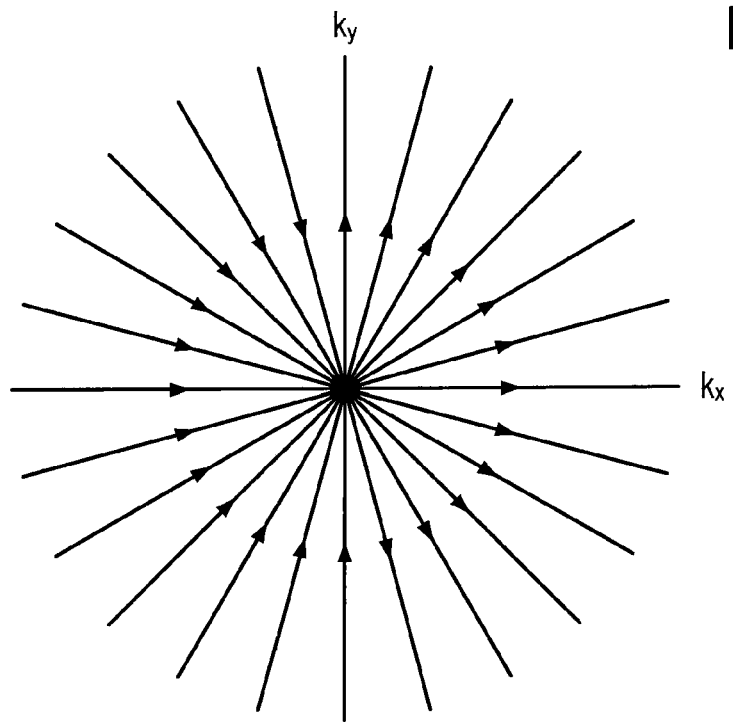
FIG. 2B is a graphic illustration of the manner in which k-space is sampled during a typical projection reconstruction image acquisition using an MRI system.

Generally speaking, the method of reconstructing an image from a set of data includes a series of numerical steps to estimate a desired image, I, from the measured data samples, Y. More specifically, the image reconstruction should fulfill the following consistency condition:

$$AI=Y, \quad (1)$$

where A is a system matrix. In general, the system matrix, A, can be viewed as a forward projection operator that relates the desired image, I, to the acquired data samples, Y. When dealing with computed tomography (CT) imaging, the system matrix can include a reprojection operation, while in magnetic resonance imaging (MRI), it can include a Fourier transform operation. The consistency condition of equation (1), put in other words, states that when an image is faithfully reconstructed, the forward operation should substantially mimic the actual data acquisition procedure in order to generate a correct estimate of the measured projection data.

Turning now to the method of the present invention, a method for reconstructing a quality desired image is provided. In general, a "prior image" is employed to constrain an iterative image reconstruction method, in which the principles of compressed sensing (CS) are utilized. For example, in addition to the sparsifying transforms commonly used in CS, an image is further sparsified by subtracting the prior image from the desired image. As a result, an image can be accurately reconstructed using a substantially fewer number of samples than required by CS methods.

More specifically, given a prior image, $I_P$, and a desired image to be reconstructed, I, the method of the present invention for image reconstruction is implemented by minimizing the following objective function:

$$\alpha\|\Psi_1(I-I_P)\|_1+(1-\alpha)\|\Psi_2 I\|_1, \quad (2)$$

where $\Psi_1$ and $\Psi_2$ are sparsifying transforms, $\|\ldots\|_1$ is an $L_1$-norm operation, and $\alpha$ is a regularization parameter that is utilized to control the relative weight of the two terms in the objective function of equation (2). As noted above, $$\|x\|_1 = \sum_{i=1}^{N} |x_i|,$$

indicates the $L_1$-norm of an N-dimensional vector, x. More generally, a deviation from the true $L_1$-norm is possible while still maintaining adequate image quality in the desired image. For example, the objective function of equation (2) can be generalized as:

$$\alpha\|\Psi_1(I-I_P)\|_p+(1-\alpha)\|\Psi_2 I\|_p,$$

where $\|\ldots\|_p$ is an $L_p$-norm operation having the form:

$$\|x\|_p = \left(\sum_{i=1}^{N} |x_i|^p\right)^{1/p}.$$

As noted above, preferably p=1.0; however, in the alternative, different values of p are possible. It should be appreciated by those skilled in the art that the further the value of p deviates from p=1.0, generally, the more degradation will be evident in the reconstructed desired image.

The sparsifying transforms in equation (2), $\Psi_1$ and $\Psi_2$, are, in general, different; however, in the alternative, $\Psi_1$ and $\Psi_2$ may be the same sparsifying transform. Exemplary sparsifying transforms include a wavelet transform, a first order finite difference, a second order finite difference, and a discrete gradient transform, such as, for example, a discrete gradient transform, $\nabla_{m,n}$, having the following form:

$$\nabla_{m,n} I(m,n) = \sqrt{[I(m+1,n) - I(m,n)]^2 + [I(m,n+1) - I(m,n)]^2},$$ (5)

where the indices m and n indicate the location of a pixel in an image, I. The image specified as $\nabla_{m,n}I(m,n)$ is commonly referred to as the "gradient image".

Both of the terms in the objective function of equation (2) are important. As a result of their importance, the selection of the regularization parameter, $\alpha$, is utilized to control the overall image reconstruction process. Therefore, the selection of the regularization parameter, $\alpha$, will depend on the choice of the prior image, $I_P$, and also the clinical application at hand. For example, the second term in the objective function of equation (2), $(1-\alpha)\|\Psi_2 I\|_1$, mitigates streaking artifacts that are potentially inherited from the prior image, $I_P$. For further example, selecting a regularization parameter of $\alpha \approx 0.3$-$0.7$ is generally sufficient for cardiac imaging applications.

To better incorporate the consistency condition of equation (1) into the overall image reconstruction, the method of Lagrange multipliers is utilized. In such a manner, the consistency condition is employed to add a further constraint on the minimization of the objective function set forth in equation (2). A new objective function is thus produced, which has the form:

$$\alpha\|\Psi_1(I-I_P)\|_1 + (1-\alpha)\|\Psi_2 I\|_1 + \lambda\|X\|_2^2,$$ (3)

where $\lambda$ is the Lagrange multiplier, X is a difference matrix, and $\|\ldots\|_2^2$ is a squared $L_2$-norm operation, which, for an N-dimensional vector, x, has the form:

$$\|x\|_2^2 = \sum_{i=1}^{N} x_i^2.$$

The difference matrix in equation (3) accounts for the consistency condition of equation (1), and has the following form:

$$X = AI - Y.$$

The Lagrange multiplier, $\lambda$, is determined empirically for the particular imaging system employed when practicing the present invention. For example, the Lagrange multiplier, $\lambda$, is determined by a pre-determined tradeoff between the desired data consistency requirement and the similarity to the prior image, $I_P$. When a large Lagrange multiplier, $\lambda$, is selected, the reconstructed image has lower noise variance; however, this may be achieved as a loss of the high spatial resolution characteristic of the prior image. Similarly, when a smaller Lagrange multiplier, $\lambda$, is used, the high spatial resolution characteristic of the prior image is well preserved, but the noise variance can be high in the desired image. Such a situation affects the contrast-to-noise ratio achievable by the imaging system utilized.

The objective function presented in equation (3) can further be altered in order to account for noise of the imaging system. In such a manner, the following objective function is minimized:

$$\alpha\|\Psi_1(I-I_P)\|_1 + (1-\alpha)\|\Psi_2 I\|_1 + \lambda(X^T D X),$$ (4)

where $X^T$ is the transpose of the difference matrix, X, and D is a system noise matrix, which is a diagonal matrix having the following matrix elements:

$$D_{ij} = \begin{cases} \frac{1}{\sigma_n^2} & \text{if } i = j \\ 0 & \text{if } i \neq j, \end{cases}$$

where $\sigma_n^2$ is the noise variance, and is a parameter indicative of noise in the imaging system employed when practicing the present invention. For example, in an x-ray imaging system, the noise parameter, $\sigma_n^2$, is the noise variance associated with the $n^{th}$ x-ray detector. Alternatively, in an MR imaging system, the noise parameter, $\sigma_n^2$, is estimated noise variance in the $n^{th}$ receiver coil.

In the method of the present invention, the prior image, $I_P$, plays two roles. First, it serves as a seed image in the iterative reconstruction, which accelerates the overall image reconstruction method. In addition, the prior image, $I_P$, is employed to further sparsify the desired image, I, and, thus, serves as yet another sparsifying transform. A brief discussion of possible prior images, $I_P$, is provided below with respect to different imaging modalities; however, it should be appreciated by those skilled in the art that prior images, $I_P$, other than those expressly described herein can be employed depending on the clinical application. As referred to herein, a prior image, $I_P$, is an image of the subject that includes a priori information indicative of the desired image to be reconstructed. The prior image, $I_P$, can be from a previously performed imaging study, or can be reconstructed from image data acquired in the same session as the image data acquired for the desired images. Typically, the prior image, $I_P$, is acquired using the same imaging modality as the desired images; however, as will be described below, there are applications where the prior image, $I_P$, can be obtained from a different imaging modality than the desired images.

Figure 3:
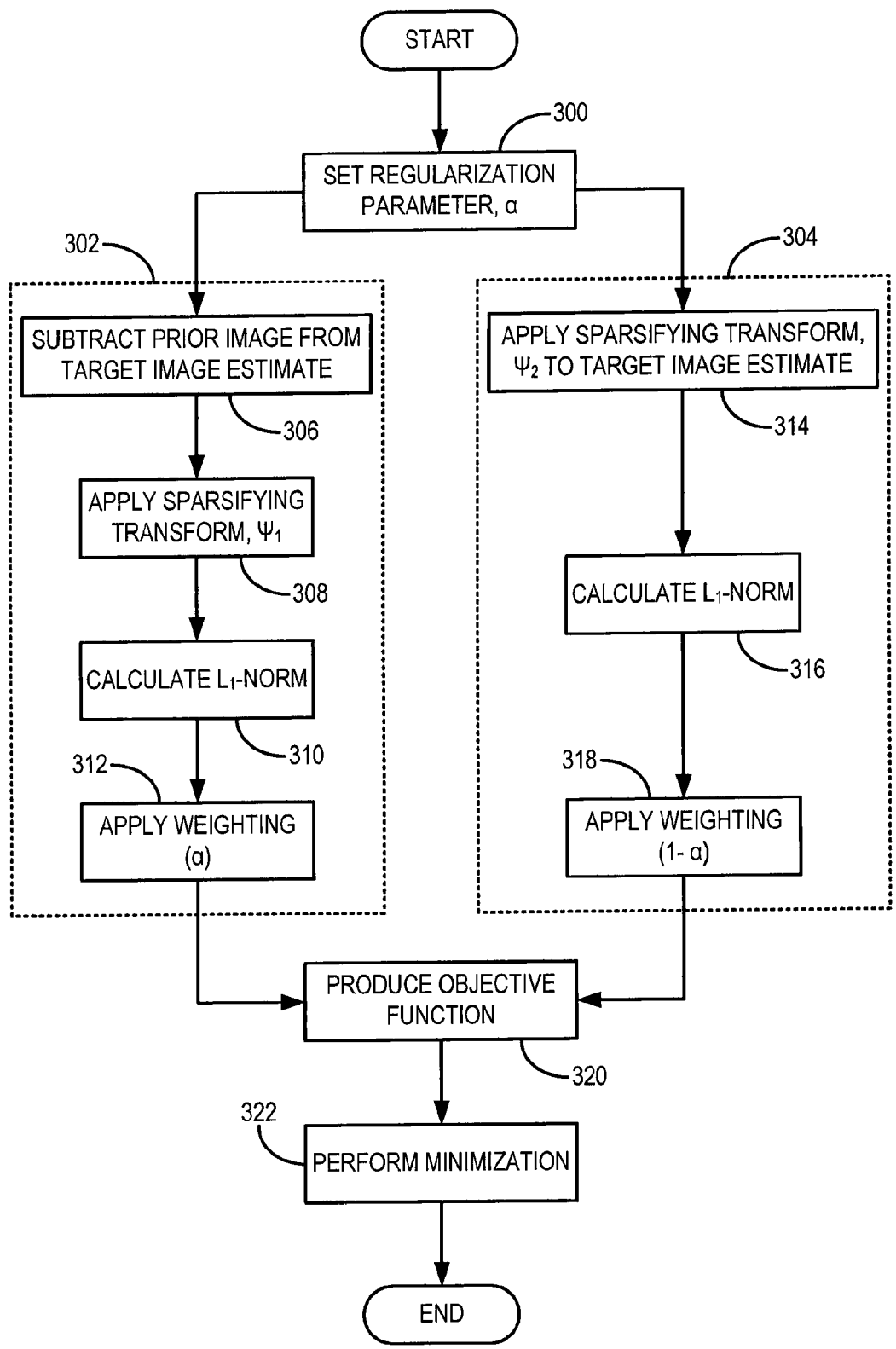
FIG. 3 is a flowchart an embodiment of the image reconstruction method of the present invention.

With reference now to FIG. 3, one implementation of the method of the present invention employs the objective function of equation (2), and begins by initializing the regularization parameter, $\alpha$, as indicated at step 300. The choice of the regularization parameter, $\alpha$, determines the trade-off between the sparsity of the desired image, and the influence of the prior image on the desired image. Accordingly, the value of the regularization parameter, $\alpha$, will vary depending on the clinical application at hand. For example, a value of $\alpha \approx 0.3$-$0.7$ is generally sufficient for cardiac imaging applications. Subsequently, the first and second terms in the objective function of equation (2) are initialized, as indicated in steps 302 and 304, respectively. The initialization of the first term, $\alpha\|\Psi_1(I-I_P)\|_1$, begins at step 306 where the prior image, $I_P$, is subtracted from an estimate of the desired image, I, to produce a "difference image". The particular choice of the prior image, $I_P$, and the estimate of the desired image, I, will depend on the imaging modality and the particular clinical application. Accordingly, different alternatives for these choices will be discussed in detail below. The difference image is subsequently sparsified by applying the sparsifying transform, $\Psi_1$, as indicated at step 308. As described above, the sparsifying transform, $\Psi_1$, can be any number of mathematical operations, including a wavelet transform, a first order finite difference, a second order finite difference, and a discrete gradient transform. The $L_1$-norm of this sparsified difference image is then calculated at step 310. The result of this process is then weighted by the regularization parameter, $\alpha$, as indicated at step 312.

The initialization of the second term in the objective function of equation (2), $(1-\alpha)\|\Psi_2 I\|_1$, begins at step 314 where the estimate of the desired image, I, is sparsified through the application of the sparsifying transform, $\Psi_2$. Subsequently, the $L_1$-norm of this sparsified desired image estimate is calculated at step 316. When the discrete gradient transform, $\nabla_{m,n}$, is selected as the sparsifying transform, $\Psi_2$, steps 314 and 316 can be viewed as calculating the total variation, TV, of the desired image estimate, which has the form:

$$TV(I) = \|\nabla I\|_1 = \Sigma |\nabla I|.$$

After the $L_1$-norm of the sparsified desired image estimate is calculated, the result is weighted by $(1-\alpha)$, as indicated at step 318. The objective function of equation (2) is subsequently produced in step 320 by adding the first and second terms together. This objective function is then minimized, as indicated at step 322, using, for example, a nonlinear conjugate gradient method. The minimization process proceeds until a stopping criterion is satisfied. The stopping criterion includes, for example, comparing the current estimate of the desired image with the estimate of the desired image from the previous iteration. Such a stopping criterion has the following form:

$$\sum_i \sum_j (I_{ij}^{(k+1)} - I_{ij}^{(k)})^2,$$

where, $I_{ij}^{(k+1)}$ is the value of the $(k+1)^{th}$ estimate of the desired image at the pixel location (i,j), and $I_{ij}^{(k)}$ is the value of the $k^{th}$ estimate of the desired image at the pixel location (i,j).

Figure 4:
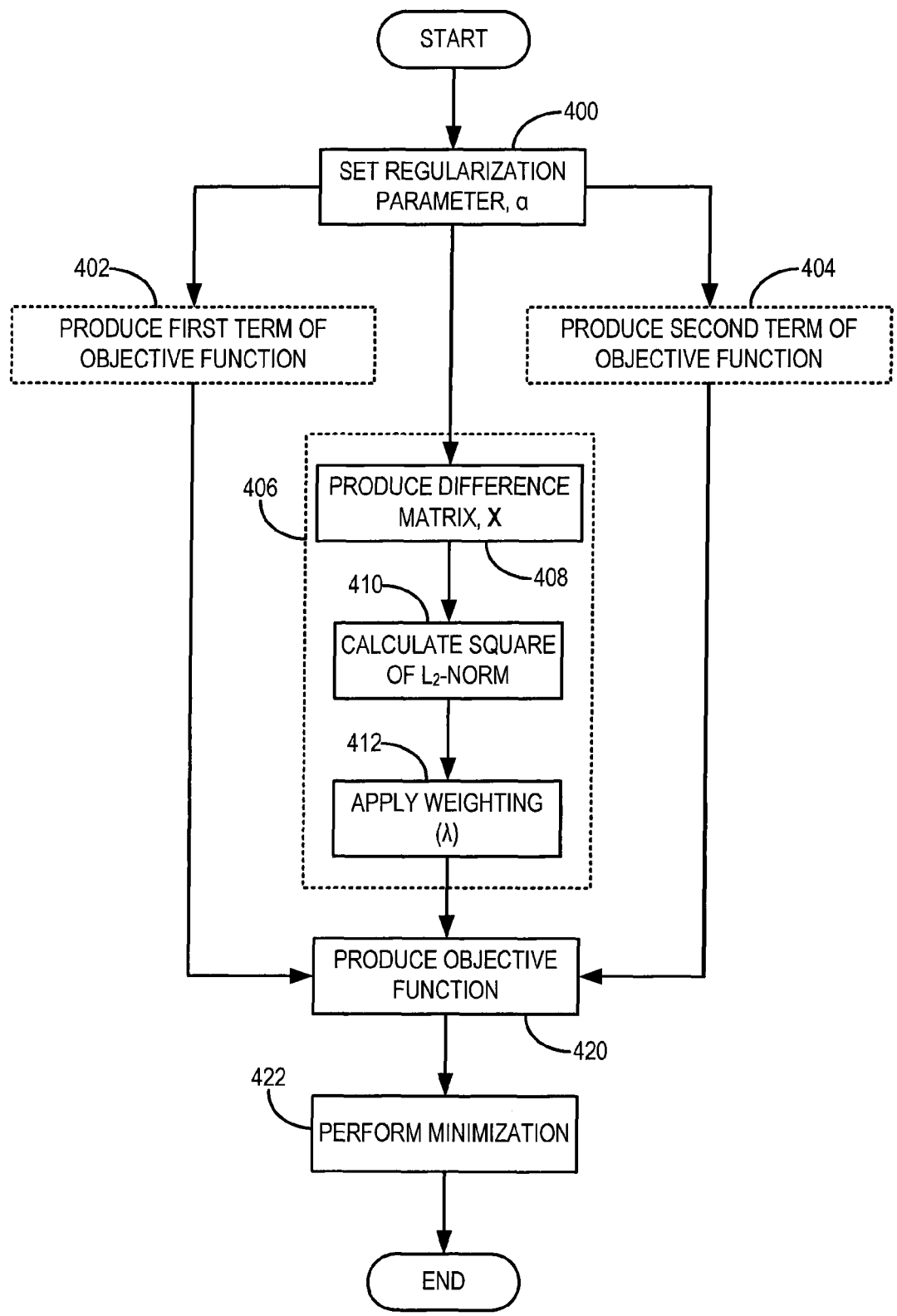
FIG. 4 is a flowchart of another embodiment of the image reconstruction method of the present invention.

With reference now to FIG. 4, another implementation of the method of the present invention employs the objective function of equation (3), and begins by initializing the regularization parameter, $\alpha$, as indicated at step 400. Subsequently, the first and second terms in the objective function of equation (3) are initialized, as indicated in steps 402 and 404, respectively. This process proceeds in the same manner as described above with reference to steps 302 and 304 in FIG. 3. Now, however, the consistency condition of equation (1) is incorporated into a third term, $\lambda \|X\|_2^2$, which is initialized at step 406. First, the difference matrix, X, is produced, as indicated at step 408. As described above in detail, the difference matrix, X, corresponds to the consistency condition of equation (1) and has the following form:

$$X = AI - Y.$$

Thus, the difference matrix is determined by applying the system matrix, A, to the estimate of the desired image, I, and subsequently subtracting the acquired image data, Y, that corresponds to the desired image. The square of the $L_2$-norm of the difference matrix, X, is calculated next at step 410. After the square of the $L_2$-norm of the difference matrix, X, has been produced, the Lagrange multiplier, $\lambda$, is determined and employed to weight the difference matrix, X, as indicated at step 412. As described above, the Lagrange multiplier is empirically determined by and the value selected by the user based on the clinical application at hand. The objective function of equation (3) is subsequently produced in step 420 by adding the first, second, and third terms together. This objective function is then minimized, as indicated at step 422, using, for example, a nonlinear conjugate gradient method. The minimization process proceeds until a stopping criterion is satisfied, as described above.

Figure 5:
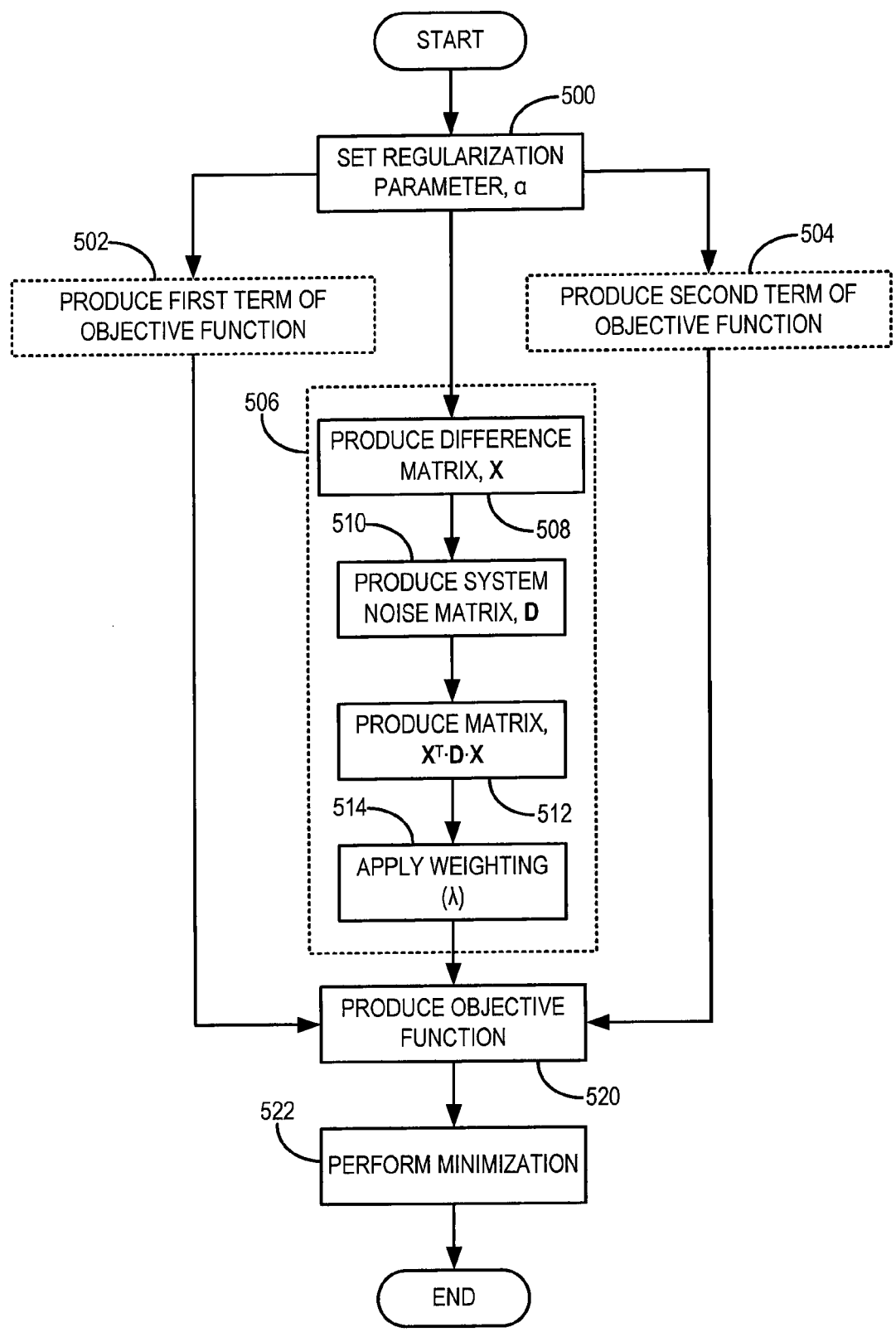
FIG. 5 is a flowchart of yet another embodiment of the image reconstruction method of the present invention.

With reference now to FIG. 5, yet another implementation of the method of the present invention employs the objective function of equation (4), and begins by initializing the regularization parameter, $\alpha$, as indicated at step 500. Subsequently, the first and second terms in the objective function of equation (4) are initialized, as indicated in steps 502 and 504, respectively. This process proceeds in the same manner as described above with reference to steps 302 and 304 in FIG. 3. Now, however, the consistency condition of equation (1) and the effects of noise in the imaging system are incorporated into a third term, $\lambda(X^T DX)$, which is initialized at step 506. First, the difference matrix, X, is produced, as indicated at step 508, and described above with reference to step 408 in FIG. 4. Next, a system noise matrix, D, is produced, as indicated in step 510. The system noise matrix, D, is a diagonal matrix having matrix elements determined in accordance with the following:

$$D_{ij} = \begin{cases} \frac{1}{\sigma_n^2} & \text{if } i = j \\ 0 & \text{if } i \neq j. \end{cases}$$

As described above, $\sigma_n^2$ is the noise variance, and is a parameter indicative of noise in the imaging system employed when practicing the present invention. For example, in an x-ray imaging system, the noise parameter, $\sigma_n^2$, is the noise variance associated with the $n^{th}$ x-ray detector. Alternatively, in an MR imaging system, the noise parameter, $\sigma_n^2$, is estimated noise variance in the $n_{th}$ receiver coil.

$\sigma_n$ is a noise parameter indicative of noise in the imaging system employed when practicing the present invention. For example, in an x-ray imaging system, the noise parameter, $\sigma_n$, is the noise associated with the $n^{th}$ x-ray detector. After the system noise matrix, D, has been produced, the following matrix multiplication is performed:

$$X^T DX,$$

as indicated at step 512. The result of this operation is subsequently scaled by the Lagrange multiplier, as indicated at step 514. The objective function of equation (4) is subsequently produced in step 520 by adding the first, second, and third terms together. This objective function is then minimized, as indicated at step 522, using, for example, a nonlinear conjugate gradient method. The minimization process proceeds until a stopping criterion is satisfied, as described above.

The present invention, as described above, may be applied to many different medical imaging modalities and may be utilized in many different clinical applications. A number of such exemplary clinical applications are described below to illustrate the broad scope of the present invention. Such embodiments do not necessarily represent the full scope of the invention, however, and reference is made therefore to the claims and herein for interpreting the scope of the invention.

X-Ray Computed Tomography

The risks associated with exposure to the ionizing radiation used in medical imaging, including x-ray computed tomography (CT) and nuclear myocardial perfusion imaging (MPI), have increasingly become a great concern in recent years as the number CT and nuclear MPI studies has dramatically increased. The reported effective radiation dose from a cardiac CT angiography session is approximately 5-20 mSv for male patients and even higher for female patients. This dose is in addition to the smaller radiation dose from the calcium scoring CT scan that is routinely performed prior to intravenous contrast injection. To perform CT-MPI as part of a comprehensive cardiac CT study would require acquiring images over the same region of the heart approximately 20-30 times, resulting in an increase in radiation dose of approximately twenty- to thirty-fold, which would be an unacceptable level of radiation exposure.

Additional major limitations exist with current cardiovascular CT imaging. In particular, current cardiac CT imaging methods suffer from inadequate temporal resolution to provide high quality cardiac images in all patient subsets. Thus, improving temporal resolution with CT cardiovascular imaging enables more accurate diagnoses and potentially safer, more effective therapeutic interventions.

X-Ray Multi-Detector Computed Tomography

Despite the short gantry rotation time of current state-of-the-art multi-detector CT (MDCT) imaging systems, the temporal aperture is inadequate to accurately measure global function (ejection fraction), assess wall motion abnormalities, or freeze valve motion to assess valvular abnormalities. In general, the temporal aperture should be no longer than 40-50 milliseconds in order to accurately assess global function and local wall motion abnormalities. In addition, despite current short gantry rotation times, pharmacological intervention (e.g., the administration of beta blockers) is often needed to slow the heart rate sufficiently in order to acquire images free from motion artifacts. This presents a limitation in the use of such a method since beta blockers are contraindicated in patients with impaired heart conduction and pulmonary disease, such as asthma. These are additional barriers for wider implementation of cardiac CT angiography.

In MDCT, the temporal resolution is primarily limited by the gantry rotation speed. In order to accurately reconstruct an image, the projection data is typically acquired over an angular range of 180 degrees, and greater. This angular range covers about two-thirds of a complete circle. After the incorporation of an appropriate weighting function in the employed image reconstruction algorithm, the typical temporal aperture of MDCT is limited to 50 percent of the gantry rotation time for a complete rotation. The temporal resolution and corresponding gantry rotation speed for the state-of-the-art MDCT scanners are summarized below in Table 1.

TABLE 1

Temporal Resolution Chart

| Gantry Rotation Speed | X-ray Source Type | Temporal Resolution |
|---|---|---|
| 350 ms | Single | 175 ms |
| 350 ms | Dual | 87 ms |
| 270 ms | Single | 135 ms |

In cardiac MDCT imaging, to achieve better than 20 ms temporal resolution, around 50 millisecond gantry rotation period is required, which is currently not feasible due to mechanical limitations on the CT imaging systems. Since the gantry speed is limited, segmented reconstruction has been investigated to improve temporal resolution. In segmented reconstruction, the data coverage required for a single reconstruction is filled with projection data selected from different heartbeats at the same cardiac phase. Using segmented reconstruction, the temporal resolution may be improved.

In the best case scenario, the temporal resolution can be improved by a factor of N (where N is the number of sectors utilized). However, segmented reconstruction is highly dependent on the consistency of the heart motion from one cycle to the next. It is noted that the gantry rotates several times during a single heart beat. When multiple heart beats are needed for segmented reconstruction, the projection data are distributed over many gantry rotations. Thus, due to the possible synchronization between the gantry rotation and the heart beat, the segments selected from different heartbeats often do not combine to produce a short-scan dataset. Therefore, the union of the segmented data sets does not provide a complete projection data set for an accurate image reconstruction. As a result, the promise of temporal resolution improvement in segmented reconstruction is not reliably achieved and, thus, the segmented reconstruction method is rarely utilized in clinical practice.

X-Ray Computed Tomography Imaging System

Figure 6A:
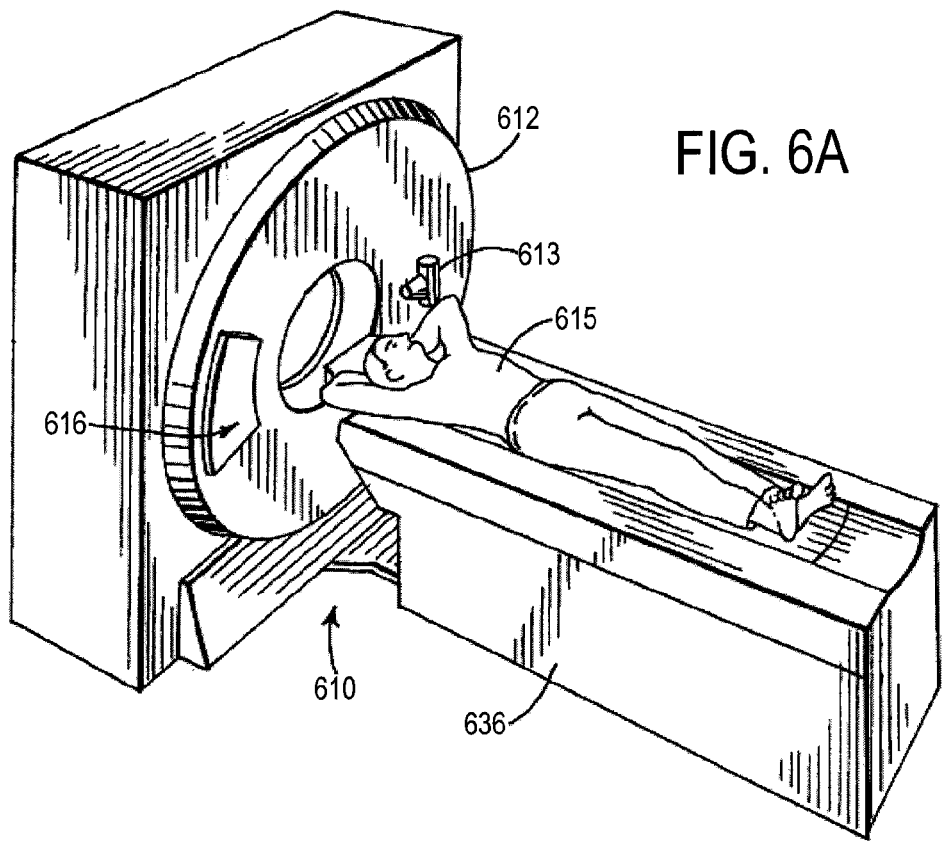
FIG. 6A is a pictorial view of an x-ray computed tomography (CT) imaging system.
Figure 6B:
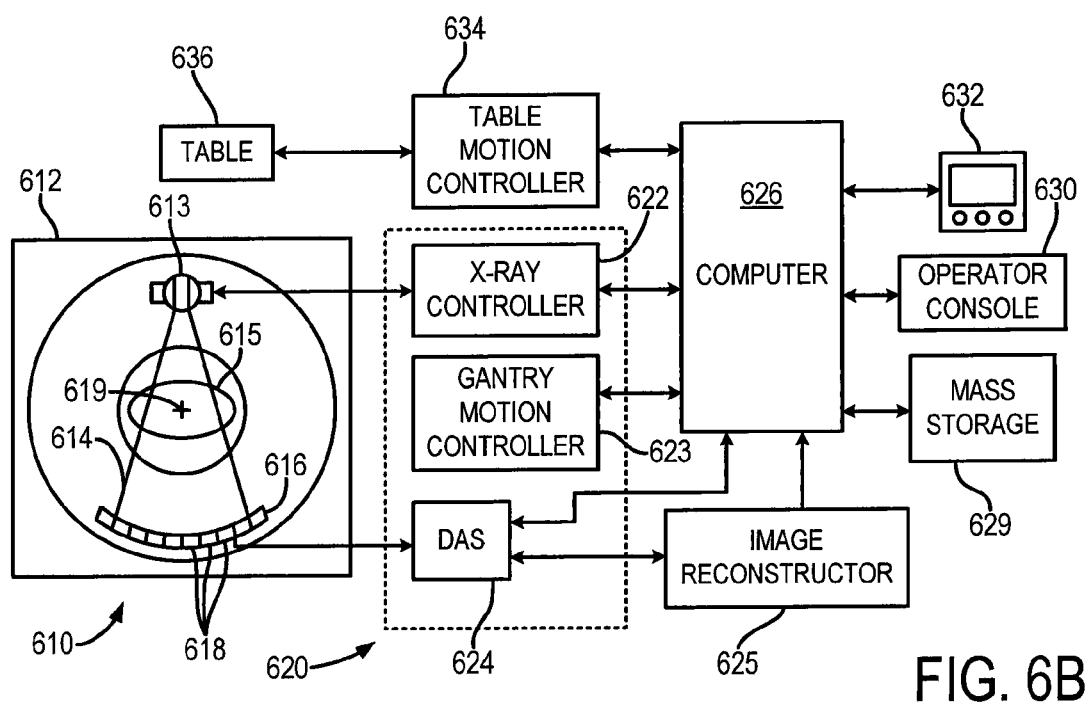
FIG. 6B is a block diagram of the CT imaging system of FIG. 6A.

With initial reference to FIGS. 6A and 6B, an x-ray computed tomography (CT) imaging system 610 includes a gantry 612 representative of a "third generation" CT scanner. Gantry 612 has an x-ray source 613 that projects a fan beam, or cone beam, of x-rays 614 toward a detector array 616 on the opposite side of the gantry. The detector array 616 is formed by a number of detector elements 618 which together sense the projected x-rays that pass through a medical patient 615. Each detector element 618 produces an electrical signal that represents the intensity of an impinging x-ray beam and hence the attenuation of the beam as it passes through the patient. During a scan to acquire x-ray projection data, the gantry 612 and the components mounted thereon rotate about a center of rotation 619 located within the patient 615.

The rotation of the gantry and the operation of the x-ray source 613 are governed by a control mechanism 620 of the CT system. The control mechanism 620 includes an x-ray controller 622 that provides power and timing signals to the x-ray source 613 and a gantry motor controller 623 that controls the rotational speed and position of the gantry 612. A data acquisition system (DAS) 624 in the control mechanism 620 samples analog data from detector elements 618 and converts the data to digital signals for subsequent processing. An image reconstructor 625, receives sampled and digitized x-ray data from the DAS 624 and performs high speed image reconstruction. The reconstructed image is applied as an input to a computer 626 which stores the image in a mass storage device 628.

The computer 626 also receives commands and scanning parameters from an operator via console 630 that has a keyboard. An associated display 632 allows the operator to observe the reconstructed image and other data from the computer 626. The operator supplied commands and parameters are used by the computer 626 to provide control signals and information to the DAS 624, the x-ray controller 622 and the gantry motor controller 623. In addition, computer 626 operates a table motor controller 634 which controls a motorized table 636 to position the patient 615 in the gantry 612.

X-Ray Computed Tomography Image Reconstruction

Figure 7A:
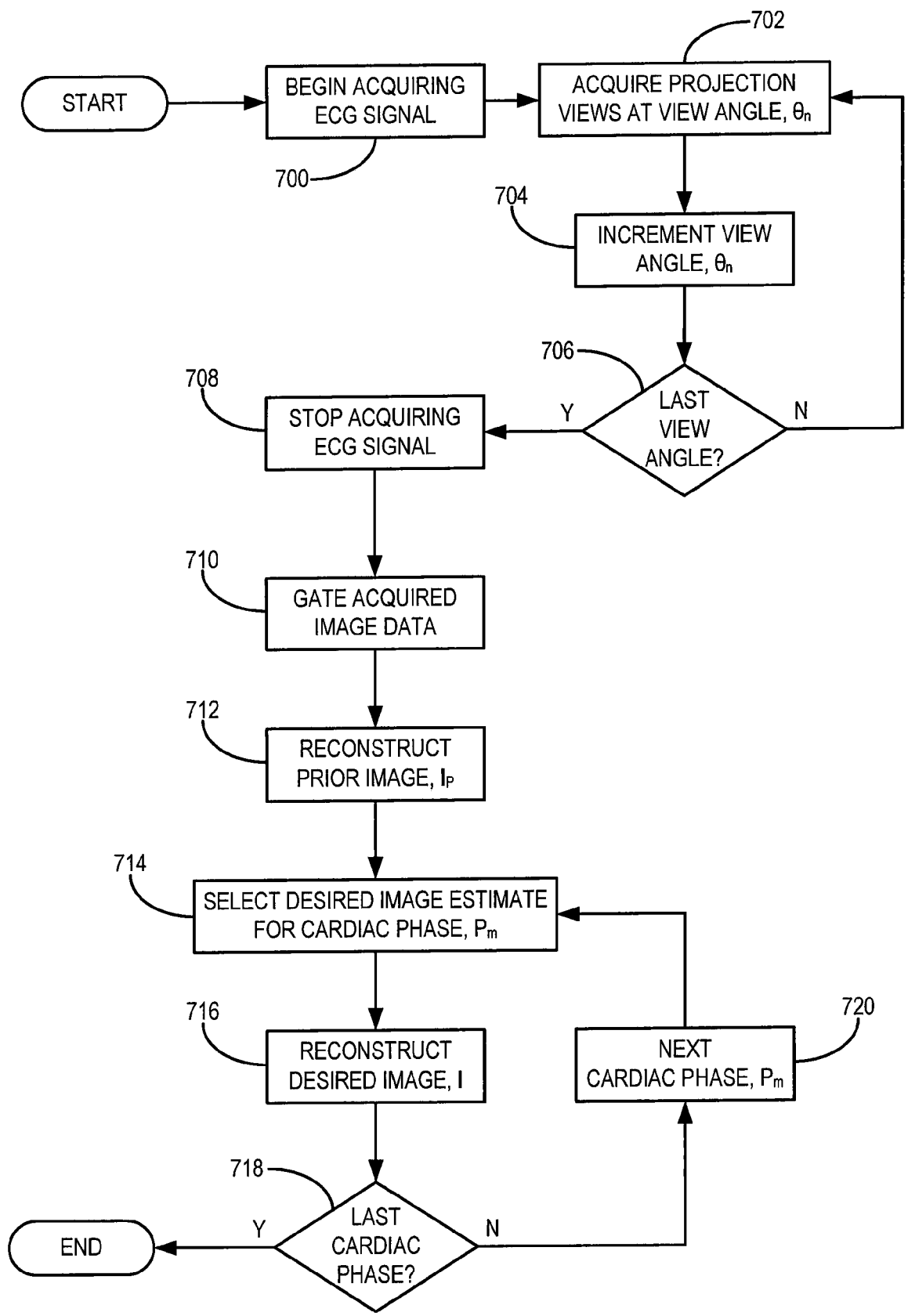
FIG. 7A is a flowchart of an embodiment of the present invention used in the CT system of FIG. 6A.
Figure 8:
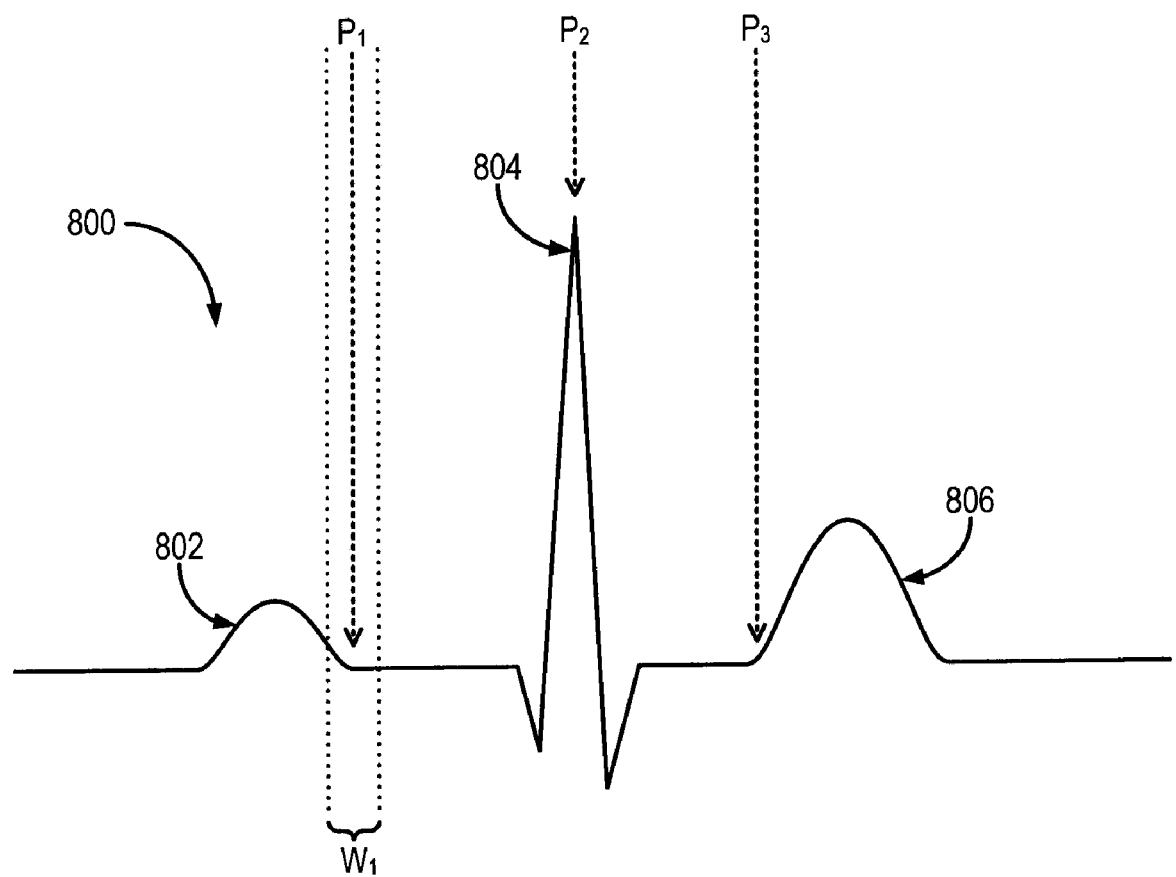
FIG. 8. is a graphic illustration of an exemplary electrocardiogram (ECG) signal.

Referring now to FIG. 7A, when practiced in a cardiac x-ray CT imaging system, the method of the present invention starts by acquiring a signal indicative of the physiological motion of the subject's heart. For example, the acquisition of an electrocardiogram (ECG) signal from the subject is initiated, as indicated at step 700. This ECG signal is used to retrospectively gate the acquired image data into M different cardiac phases, $P_M$. For example, and with reference to FIG. 8, three cardiac phases, $P_1$, $P_2$, and $P_3$ can be selected from time points in the ECG signal 800. In this example, the first cardiac phase, $P_1$, is selected as during the isovolumetric contraction phase at the end of the P wave 802; the second cardiac phase, $P_2$, is selected as the beginning of the rapid ejection phase at the peak of the QRS complex 804; and the third cardiac phase, $P_3$, is selected as the beginning of the reduced ejection phase at the beginning of the T wave 806. In general, any number of cardiac phases can be selected and from any time point in the ECG signal.

Referring again to FIG. 7A, data acquisition begins by acquiring image data in the form of a set of projection views at a first view angle, $\theta_n$, as indicated at step 702. The gantry is subsequently rotated to a new view angle at step 704. More image data is subsequently acquired at the new view angle, $\theta_{n+1}$, and this process is repeated until the gantry has been rotated to a last view angle, $\theta_N$, as indicated by decision block 706. After all of the desired image data has been acquired, the acquisition of ECG signal is stopped, as indicated at step 708. The acquired image data is subsequently gated, retrospectively, into the M different cardiac phases, $P_m$ at step 710. For example, and referring again to FIG. 8, all of the image data acquired during a first gating window, $W_1$, is selected as corresponding to the first cardiac phase, $P_1$. For example, a narrow gating window, $W_1$, of 20 milliseconds or less is employed, such that there is substantially only one view angle within the gating window. This retrospective gating produces a "cardiac phase image data set" for each of the M different desired cardiac phases. Therefore, each cardiac phase image data set includes a plurality of projection views acquired during the gating window, $W_m$, corresponding to a given cardiac phase, $P_m$. In the alternative, the original image data acquisition can be prospectively gated such that image data is only acquired at specific time points during the ECG signal. Following this data acquisition scheme, all of the image data acquired during a selected cardiac phase is similarly combined into a cardiac phase image data set.

Since each cardiac phase image data set is highly undersampled, an attempt to reconstruct images using standard image reconstruction algorithms, such as the well-known filtered backprojection (FBP) method, will result in severe streaking artifacts. Therefore, and referring again to FIG. 7A, the method of the present invention proceeds by reconstructing a prior image, $I_P$, as indicated in step 712. The prior image, $I_P$, is reconstructed at step 712 using a conventional image reconstruction method, such as the FBP method. In particular, the prior image, $I_P$, is reconstructed from all of the image data acquired over the N view angles, $\theta_n$. Such a prior image will inherently lose the dynamic information associated with the beating heart, since the image data was acquired over a plurality of different cardiac phases; however, this dynamic information can be recovered when reconstructing the desired images of each cardiac phase. In the alternative, however, the prior image, $I_P$, can be reconstructed using other image reconstruction methods such as, for example, highly constrained backprojection (HYPR), which is described in co-pending U.S. patent application Ser. No. 11/482,372; HYPR local reconstruction (HYPR-LR), which is described in co-pending U.S. patent application Ser. No. 12/032,240; and iterative HYPR (I-HYPR), which is described in co-pending U.S. patent application Ser. No. 12/032,262. By employing the HYPR-LR method, for example, a further increase in the signal-to-noise ratio (SNR) is possible in the desired image.

Proceeding with the image reconstruction method, an estimate of the desired image for a given cardiac phase, $P_m$, is subsequently produced at step 714. For example, this estimate can be an image reconstructed from the appropriate cardiac phase image data set using a FBP method. In the alternative, however, the prior image, $I_P$, can be employed. A desired image, I, of the selected cardiac phase, $P_m$, is subsequently reconstructed in accordance with the method of the present invention described above with reference to FIGS. 3, 4, and 5, as indicated in step 716. Since the prior image, $I_P$, is not a high quality image, the regularization parameter, α, is selected to mitigate the effects of the poor quality of the prior image, $I_P$. For example, a value of $\alpha \approx 0.3$-$0.7$ is employed. A desired image, I, is reconstructed for each cardiac phase, $P_m$, in this manner until an image for all of the desired cardiac phases has been reconstructed, as decided at process block 718. If all of the desired images have not been reconstructed, the method selects the next cardiac phase, $P_m$, at step 720 and proceeds with the image reconstruction method.

As an example of the above described data acquisition scheme, x-ray CT image data is acquired within a single gantry rotation and a breath-hold of around 12 seconds. For a patient having an average heart rate of 75 beats per minute (bpm), such image data is acquired over 15 heart beats. Therefore, the acquired image data is spread over these 15 heart beats, and over a single gantry rotation. This acquired image data is then retrospectively gated into different cardiac phases. For example, a narrow gating window of 20 milliseconds or less is employed, such that there is substantially only one view angle within the gating window. Thus, after gating, each cardiac phase includes only about 15 view angles. It is noted that instead of a fast gantry rotation speed, the present invention provides a method for reconstructing quality images from data acquired with a substantially reduced gantry rotation speed. When practicing the present invention in the above described manner, the temporal resolution is not determined by the gantry rotation speed. Instead, temporal resolution is determined by the temporal window for the acquisition of one cone-beam projection, which is determined by the detector readout speed for each cone-beam projection.

It should be appreciated by those skilled in the art that for the above described x-ray computed tomography image reconstruction method, many equivalents, alternatives, variations, and modifications, aside from those expressly stated, are possible and within the scope of the invention. For example, the subject's respiration can be monitored with a respiration monitoring device, such as a respiratory belt, and image data retrospectively gated based on the measured respiratory information. In this manner, motion, such as internal organ motion, can be compensated for when reconstructing images. Therefore, in general, the method of the present invention can utilize any signal indicative of subject motion to gate, or divide, acquired image data into a plurality of "motion phase image data sets".

X-Ray Multi-Detector Computed Tomography Image Reconstruction

Figure 7B:
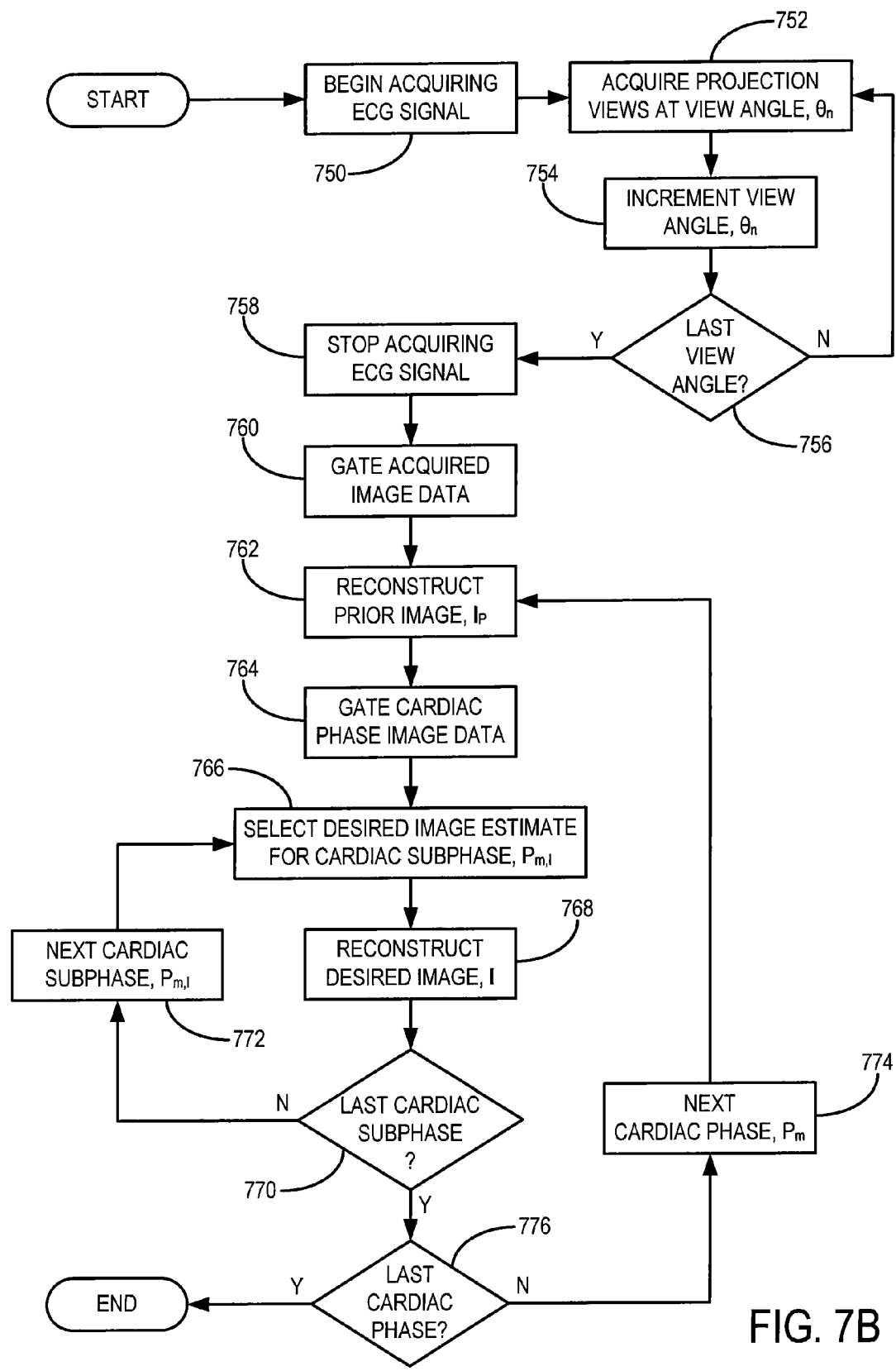
FIG. 7B is a flowchart of another embodiment of the present invention used in the CT system of FIG. 6A.

The method of the present invention is applicable not only to situations where images having high temporal resolution are reconstructed from image data acquired with a slow gantry rotation speed, but also to situations where a fast gantry rotation speed is employed. In this manner, the present invention can augment the temporal resolution of the state-of-the-art x-ray multi-detector computed tomography (MDCT) imaging systems. Referring now to FIG. 7B, when practiced in an x-ray MDCT imaging system, the method of the present invention starts by acquiring an electrocardiogram (ECG) signal from the subject, as indicated at step 750. This ECG signal is used to retrospectively gate the acquired image data into M different cardiac phases, $P_M$.

Data acquisition subsequently begins by acquiring image data in the form of a set of projection views at a first view angle, $\theta_n$, as indicated at step 752. The gantry is subsequently rotated to a new view angle at step 754. More image data is acquired at the new view angle, $\theta_{n+1}$, and this process is repeated until the gantry has been rotated to a last view angle, $\theta_N$, as determined at decision block 756. After all of the desired image data has been acquired, the acquisition of the ECG signal is stopped, as indicated at step 758. The acquired image data is subsequently gated, retrospectively, into the M different cardiac phases, $P_m$, in step 760. For example, and referring again to FIG. 8, all of the image data acquired during a first gating window, $W_1$, is selected as corresponding to the first cardiac phase, $P_1$. For example, in the state-of-the-art MDCT imaging systems, a gating window, $W_1$, of 150 milliseconds or less is employed. Such a gating window results corresponds, for example, to a duration of time during which the x-ray tube travels through an angular range of about 240 degrees (180 degrees plus the fan angle), which is the so-called short scan angular range. Thus, there are N≈640 view angles within the gating window. This retrospective gating produces a "cardiac phase image data set" for each of the M different desired cardiac phases. Therefore, each cardiac phase image data set includes a plurality of projection views acquired during the gating window, $W_m$, corresponding to a given cardiac phase, $P_m$. In the alternative, the original image data acquisition can be prospectively gated such that image data is only acquired at specific time points during the ECG signal. Following this data acquisition scheme, all of the image data acquired during a selected cardiac phase is similarly combined into a cardiac phase image data set.

Since each cardiac phase image data set (240 degree angular range and 640 projection view angles) is sufficient sampled for accurate image reconstruction, standard image reconstruction methods, such as the well-known filtered backprojection (FBP) method can employed to reconstruct images. However, due to the limited cardiac window width, $W_1$, the temporal resolution of the reconstructed images is limited to about half of the gantry rotation time. This fact is the underlying reason for the temporal resolution values presented above in Table I. Therefore, the present invention proceeds to increase temporal resolution several fold without changing of gantry rotation speed. Specifically, and referring again to FIG. 7B, the method of the present invention proceeds by reconstructing a prior image, $I_P$, as indicated in step 762. The prior image, $I_P$, is reconstructed at step 762 using a conventional image reconstruction method, such as the FBP method. In particular, the prior image, $I_P$, is reconstructed from all of the image data acquired over the N view angles, $\theta_n$, within the gating window $W_1$.

The regular gating window with width $W_1$ is then divided into a total of L narrower subwindows, or "time windows", each with a width $W_1/L$, and the cardiac phase image data sets are further gated with these subwindows, as indicated at step 764. For example, the value of L can be selected to be 2, 3, or 4 such that the gating window, $W_1$, is divided into 2, 3, or 4 equal sections, respectively. Moreover, these values correspond to an increase in temporal resolution by a factor of 2, 3, or 4. For each subwindow, the projection view angle range is reduced by a factor of L. For example, the typical angular range corresponding to the regular cardiac window width is around 240 degree. After dividing the gating window into two subwindows, however, the angular range is 120 degrees for each subdivided cardiac phase image data set, or "cardiac subphase" image data set. Thus, the conventional image reconstruction methods, such as FBP method, cannot be employed to accurately reconstruct cardiac images from the cardiac subphase image data sets. The present invention is therefore applied to accurately reconstruct cardiac images for the L cardiac subwindows.

Proceeding with the image reconstruction method, an estimate of the desired image for a given cardiac subphase, $P_{m,l}$ (l=1, 2, . . . L), is subsequently selected at step 766. For example, this estimate can be an image reconstructed from the appropriate cardiac phase image data set using a FBP method. In the alternative, however, the prior image, $I_P$, can be employed. A desired image, I, of the selected cardiac subphase, $P_{m,l}$, is subsequently reconstructed in accordance with the method of the present invention described above with reference to FIGS. 3, 4, and 5, as indicated in step 770. Since the prior image, $I_P$, is not a high temporal resolution image, some motion blurring and motion streaks appear in the prior image, $I_P$. Thus, the regularization parameter, $\alpha$, is appropriately selected to mitigate the effects of the poor temporal resolution of the prior image, $I_P$. For example, a value of $\alpha \approx 0.5$-$0.8$ is employed. A desired image, I, is reconstructed for each cardiac subphase, $P_{m,l}$, in this manner until an image for all of the desired cardiac subphases has been reconstructed, as determined at decision block 770. If all of the desired images have not been reconstructed, the method selects the next sub-cardiac phase, $P_{m,l}$, at step 772 and proceeds with the image reconstruction method. After all of the cardiac subphase images have been reconstructed for a given cardiac phase, $P_{m,l}$, a new cardiac phase is selected at step 774 and the above process repeated until all of the regular cardiac phases, $P_m$, have been utilized, as determined at decision block 776.

It should be appreciated by those skilled in the art that for the above described x-ray multi-detector computed tomography image reconstruction method, many equivalents, alternatives, variations, and modifications, aside from those expressly stated, are possible and within the scope of the invention. For example, the above described method for reconstructing higher temporal resolution images using a lower temporal resolution prior image can be iteratively implemented to generate higher and higher temporal resolution images. Also for example, the subject's respiration can be monitored with a respiration monitoring device, such as a respiratory belt, and image data retrospectively gated based on the measured respiratory information. In this manner, motion, such as internal organ motion, can be compensated for when reconstructing images. Therefore, in general, the method of the present invention can utilize any signal indicative of subject motion to gate, or divide, acquired image data into a plurality of "motion phase image data sets". Moreover, each gating window can be divided into a plurality of "time windows" such that a "motion subphase image data set" can be produced by dividing the motion phase image data set based on the time windows.

C-Arm X-Ray Imaging

Angiography C-arm systems have been modified by several vendors to enable cone-beam CT data acquisitions that provide soft tissue contrast for improved image guidance directly in an interventional suite. This represents a major advancement over the conventional rotational angiography data acquisition where only high contrast iodine filled vessels are reconstructed. Due to the slow gantry rotation speed, C-arm cone-beam CT is primarily applied in neuro-interventional procedures.

High quality non-invasive cardiac imaging is vitally important for safe and effective catheter-based interventions, specifically for pre-procedural planning, intra-procedural guidance, and post-procedural follow-up. The majority of catheter-based procedures are performed with x-ray fluoroscopic (XRF) guidance, which offers reduced information due to the limited 2D projection imaging. A further, and major, limitation when using standard XRF is poor depiction of complex 3D anatomic structures, such as, for example, blood vessels and cardiac chambers. In response to this limitation, 3D modalities such as MRI, CT, 3D ultrasound, and electromagnetic navigation systems merged with XRF are currently under investigation. Despite this fact, accurate 3D-to-2D image registration remains a major challenge. Two major interventional applications deserve emphasis for they require superior image guidance. First, percutaneous coronary artery intervention (PCI) for obstructive atherosclerosis, and second, pulmonary vein isolation (PVI) for paroxysmal atrial fibrillation. Under these conditions, the same imaging system that acquires high quality 3D tomographic images could default to real-time fluoroscopy mode to enable immediate catheter based interventions. Immediately acquired and automatically registered time-resolved 3D tomographic images could facilitate improved procedural guidance, and may ultimately reduce ionizing radiation dose, and nephrotoxic contrast dose for certain interventions. Additionally, pre-procedural, intra-procedural, and post-procedural 3D cardiac cone-beam CT evaluation could be easily performed. The gantry rotation period in a typical interventional suite is slow (5-10 seconds), and therefore, it prevents one from obtaining high temporal resolution using the conventional cardiac CT imaging paradigm.

C-Arm X-Ray Imaging System

Figure 9A:
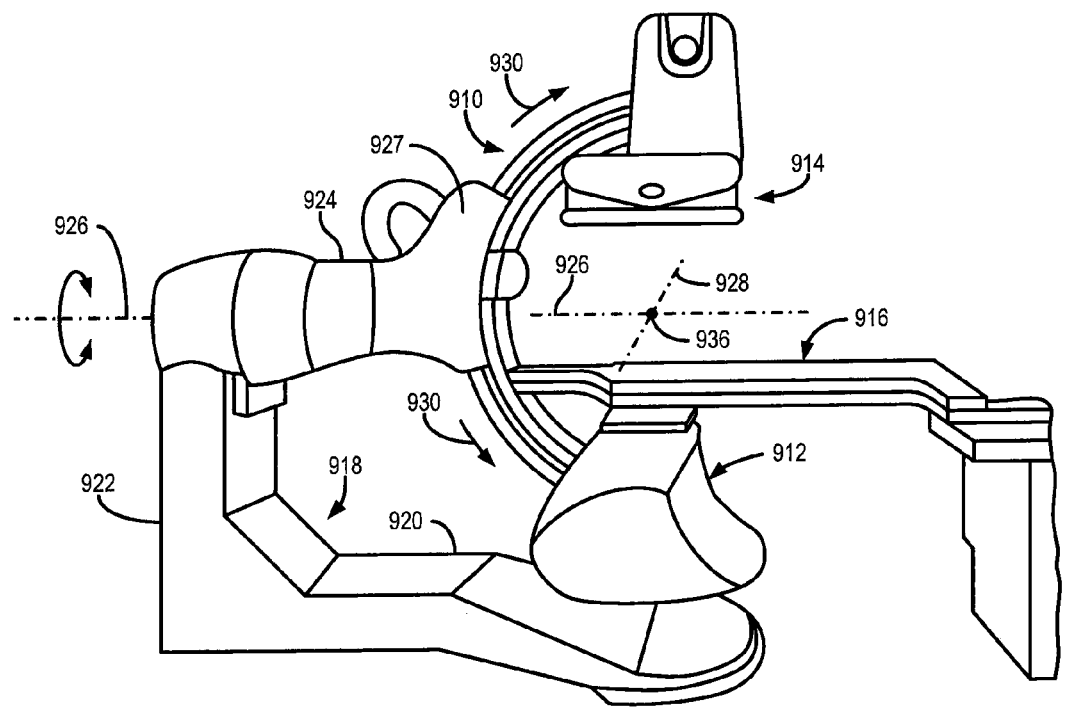
FIG. 9A is a pictorial view of a C-arm x-ray system which employs the present invention.
Figure 9B:
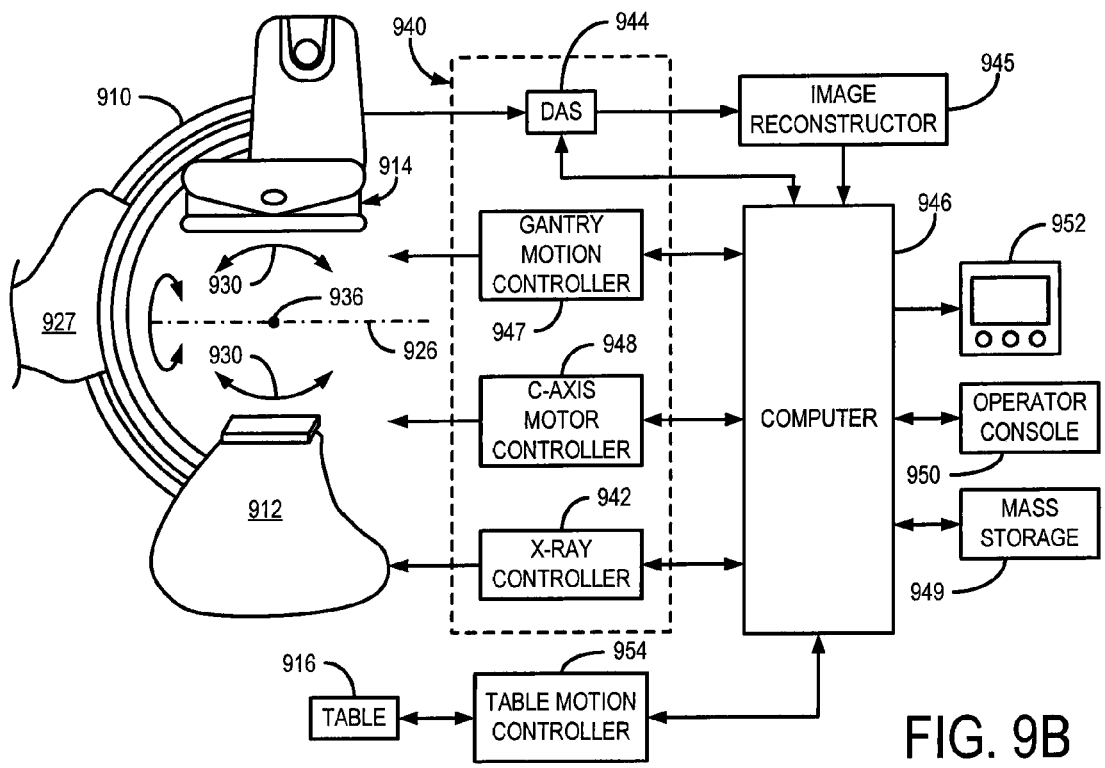
FIG. 9B is a block diagram of the C-arm x-ray system of FIG. 9A.

Referring particularly to FIGS. 9A and 9B, an embodiment of the invention employed to reconstruct images employs an x-ray system that is designed for use in connection with interventional procedures. It is characterized by a gantry having a C-arm 910 which carries an x-ray source assembly 912 on one of its ends and an x-ray detector array assembly 914 at its other end. The gantry enables the x-ray source 912 and detector 914 to be oriented in different positions and angles around a patient disposed on a table 916, while enabling a physician access to the patient.

The gantry includes an L-shaped pedestal 918 which has a horizontal leg 920 that extends beneath the table 916 and a vertical leg 922 that extends upward at the end of the horizontal leg 920 that is spaced from of the table 916. A support arm 924 is rotatably fastened to the upper end of vertical leg 922 for rotation about a horizontal pivot axis 926. The pivot axis 926 is aligned with the centerline of the table 916 and the arm 924 extends radially outward from the pivot axis 926 to support a C-arm drive assembly 927 on its outer end. The C-arm 910 is slidably fastened to the drive assembly 927 and is coupled to a drive motor (not shown) which slides the C-arm 910 to revolve it about a C-axis 928 as indicated by arrows 930. The pivot axis 926 and C-axis 928 intersect each other at an isocenter 936 located above the table 916 and they are perpendicular to each other.

The x-ray source assembly 912 is mounted to one end of the C-arm 910 and the detector array assembly 914 is mounted to its other end. As will be discussed in more detail below, the x-ray source 912 emits a cone beam of x-rays which are directed at the detector array 914. Both assemblies 912 and 914 extend radially inward to the pivot axis 926 such that the center ray of this cone beam passes through the system isocenter 936. The center ray of the cone beam can thus be rotated about the system isocenter around either the pivot axis 926 or the C-axis 928, or both during the acquisition of x-ray attenuation data from a subject placed on the table 916.

Figure 10A:
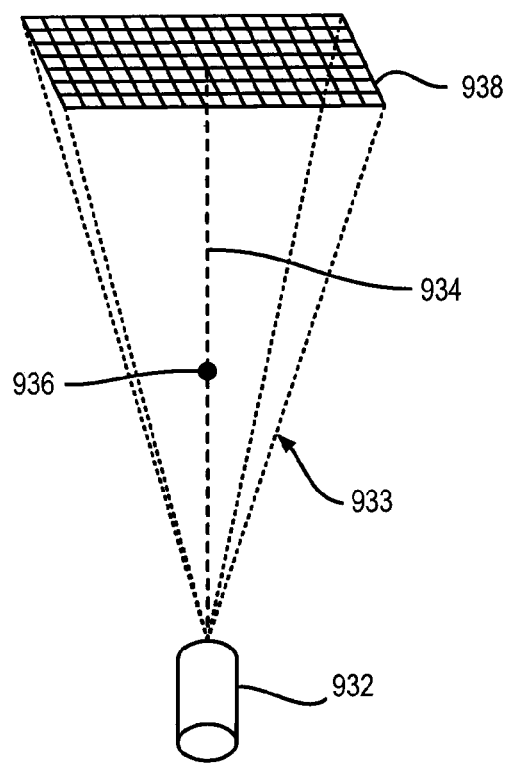
FIG. 10A is a pictorial view of the x-ray source and detector in the C-arm x-ray system of FIG. 9A.
Figure 10B:
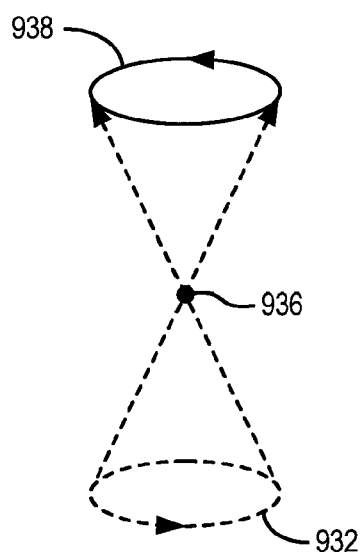
FIG. 10B is a pictorial view of the C-arm scan path employed by the C-arm x-ray system of FIG. 9A.

As shown in FIG. 10A, the x-ray source assembly 912 contains an x-ray source 932 which emits a cone beam 933 of x-rays when energized. The center ray 934 passes through the system isocenter 936 and impinges on a two-dimensional flat panel digital detector 938 housed in the detector assembly 914. The detector 938 is a 2048 by 2048 element two-dimensional array of detector elements having a size of 41 cm by 41 cm. Each element produces an electrical signal that represents the intensity of an impinging x-ray and hence the attenuation of the x-ray as it passes through the patient. During a scan the x-ray source 932 and detector array 938 are rotated about the system isocenter 936 to acquire x-ray attenuation projection data from different angles. The detector array is able to acquire 30 projections, or views, per second and this is the limiting factor that determines how many views can be acquired for a prescribed scan path and speed.

Referring particularly to FIG. 9B, the rotation of the assemblies 912 and 914 and the operation of the x-ray source 932 are governed by a control mechanism 940 of the CT system. The control mechanism 940 includes an x-ray controller 942 that provides power and timing signals to the x-ray source 932. A data acquisition system (DAS) 944 in the control mechanism 940 samples data from detector elements 938 and passes the data to an image reconstructor 945. The image reconstructor 945, receives digitized x-ray data from the DAS 944 and performs high speed image reconstruction according to the methods of the present invention. The reconstructed image is applied as an input to a computer 946 which stores the image in a mass storage device 949 or processes the image further.

The control mechanism 940 also includes pivot motor controller 947 and a C-axis motor controller 948. In response to motion commands from the computer 946 the motor controllers 947 and 948 provide power to motors in the x-ray system that produce the rotations about respective pivot axis 926 and C-axis 928. A program executed by the computer 946 generates motion commands to the motor drives 947 and 948 to move the assemblies 912 and 914 in a prescribed scan path.

The computer 946 also receives commands and scanning parameters from an operator via console 950 that has a keyboard and other manually operable controls. An associated cathode ray tube display 952 allows the operator to observe the reconstructed image and other data from the computer 946. The operator supplied commands are used by the computer 946 under the direction of stored programs to provide control signals and information to the DAS 944, the x-ray controller 942 and the motor controllers 947 and 948. In addition, computer 946 operates a table motor controller 954 which controls the motorized table 916 to position the patient with respect to the system isocenter 936.

As shown in FIG. 10D, this scan path is performed by simultaneously operating the pivot axis motor controller 847 and C-axis motor controller 849 to move the x-ray source 832 in a circular or elliptical orbit below the isocenter 936 and the detector 938 in a corresponding circular orbit above the isocenter 936. The size of the circular orbit is determined by a number of factors, but the objective is to make the enclosed area of the path as large as possible. The constraining factor is that the gantry should move through the entire circular path to acquire a single tomosynthesis data set at the frame rate needed to capture the dynamic changes that occur during the inflow of contrast agent. In this embodiment of the invention up to 10 image data sets are acquired in this manner.

C-Arm X-Ray Image Reconstruction

As described above, the same x-ray C-arm imaging system can be employed to acquire high quality 3D tomographic images and real-time fluoroscopy images to enable immediate catheter based interventions, as further described, for example, in U.S. Pat. No. 7,218,702. In this manner, time-resolved 3D tomographic images are immediately acquired and automatically registered to facilitate improved procedural guidance. This not only reduces ionizing radiation dose, but also nephrotoxic contrast dose for certain interventions. Moreover, this capability allows for pre-procedural, intra-procedural, and post-procedural 3D cardiac cone-beam CT evaluation performed as described.

Figure 11:
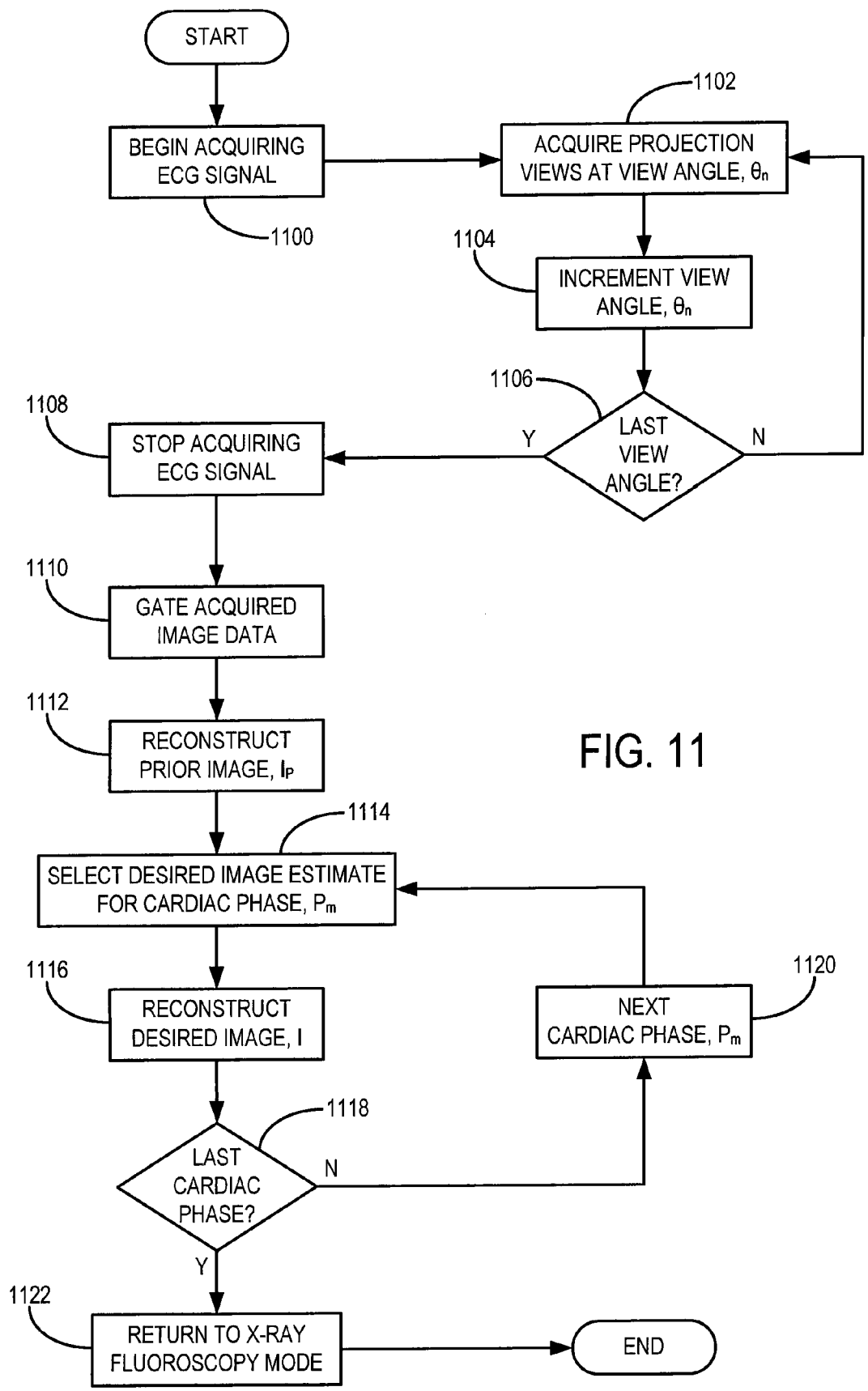
FIG. 11 is a flowchart of another embodiment of the present invention in a scan performed by the C-arm x-ray imaging system of FIG. 9A.

Accordingly, when practiced in an x-ray C-arm imaging system, the method of the present invention proceeds similar to the manner as described above with reference to FIG. 7A. Referring particularly to FIG. 11, when operating in a 3D computed tomography mode, the method starts by acquiring an electrocardiogram (ECG) signal from the subject, as indicated at step 1100. This ECG signal is used to retrospectively gate the acquired image data into M different cardiac phases, $P_M$. Data acquisition subsequently begins by acquiring image data in the form of a set of projection views at a first view angle, $\theta_n$, as indicated at step 1102. The gantry is subsequently rotated to a new view angle at step 1104, where image data is then acquired. This process is repeated until the gantry has been rotated to a last view angle, $\theta_N$, as indicated by decision block 1106. After all of the desired image data has been acquired, the acquisition of the ECG signal is stopped, as indicated at step 1110. The acquired image data is subsequently gated, retrospectively, into the M different cardiac phases, $P_m$, as described above in detail. This retrospective gating produces a "cardiac phase image data set" for each of the M different desired cardiac phases. Therefore, each cardiac phase image data set includes a plurality of projection views acquired during the gating window, $W_m$, corresponding to a given cardiac phase, $P_m$. In the alternative, the original image data acquisition can be prospectively gated such that image data is only acquired at specific time points during the ECG signal. Following this data acquisition scheme, all of the image data acquired during a selected cardiac phase is similarly combined into a cardiac phase image data set.

Since each cardiac phase image data set is highly undersampled, an attempt to reconstruct images using standard image reconstruction algorithms, such as the well-known filtered backprojection (FBP) method, will result in severe streaking artifacts. Therefore, the method of the present invention proceeds by reconstructing a prior image, $I_P$, as indicated in step 1110. The prior image, $I_P$, is reconstructed at step 1112 using a conventional image reconstruction method, such as the FBP method. In particular, the prior image, $I_P$, is reconstructed from all of the image data acquired over the N view angles, $\theta_n$. Such a prior image will inherently lose the dynamic information associated with the beating heart, since the image data was acquired over a plurality of different cardiac phases; however, this dynamic information is recovered when reconstructing the desired images of each cardiac phase. In the alternative, however, the prior image, $I_P$, can be reconstructed using other image reconstruction methods such as, for example, HYPR, HYPR-LR, and I-HYPR. By employing the HYPR-LR method, for example, a further increase in the signal-to-noise ratio (SNR) is possible in the desired image.

Proceeding with the image reconstruction method, an estimate of the desired image for a given cardiac phase, $P_m$, is produced at step 1114. For example, this estimate can be an image reconstructed from the appropriate cardiac phase image data set using a FBP method. In the alternative, however, the prior image, $I_P$, can be employed. A desired image, I, of the selected cardiac phase, $P_m$, is subsequently reconstructed in accordance with the method of the present invention described above with reference to FIGS. 3, 4, and 5, as indicated in step 1116. Since the prior image, $I_P$, is not a high quality image, the regularization parameter, $\alpha$, is selected to mitigate the effects of the poor quality of the prior image, $I_P$. For example, a value of $\alpha \approx 0.3$-$0.7$ is employed. A desired image, I, is reconstructed for each cardiac phase, $P_m$, in this manner until an image for all of the desired cardiac phases has been reconstructed, as decided at process block 1118. If all of the desired images have not been reconstructed, the method selects the next cardiac phase, $P_m$, at step 1120 and proceeds with the image reconstruction method.

When the 3D tomographic imaging is completed, the x-ray C-arm imaging system is returned to an x-ray fluoroscopic imaging mode, as indicated at step 1122. An interventional procedure, such as a cardiac catheterization procedure, can subsequently be performed with increased image guidance from the high quality 3D tomographic images reconstructed using the method of the present invention. Since the subject is not physically moved from one imaging system to the next, the imaging volumes of the 3D tomographic images and the subsequently acquired 2D x-ray fluoroscopic images are automatically registered. This provides an increase in reliability of CT image guided interventional procedures.

It should be appreciated by those skilled in the art that for the above described x-ray C-arm image reconstruction method, many equivalents, alternatives, variations, and modifications, aside from those expressly stated, are possible and within the scope of the invention. For example, the subject's respiration can be monitored with a respiration monitoring device, such as a respiratory belt, and image data retrospectively gated based on the measured respiratory information. In this manner, motion, such as internal organ motion, can be compensated for when reconstructing images. Therefore, in general, the method of the present invention can utilize any signal indicative of subject motion to gate, or divide, acquired image data into a plurality of "motion phase image data sets".

Magnetic Resonance Imaging System

Figure 12:
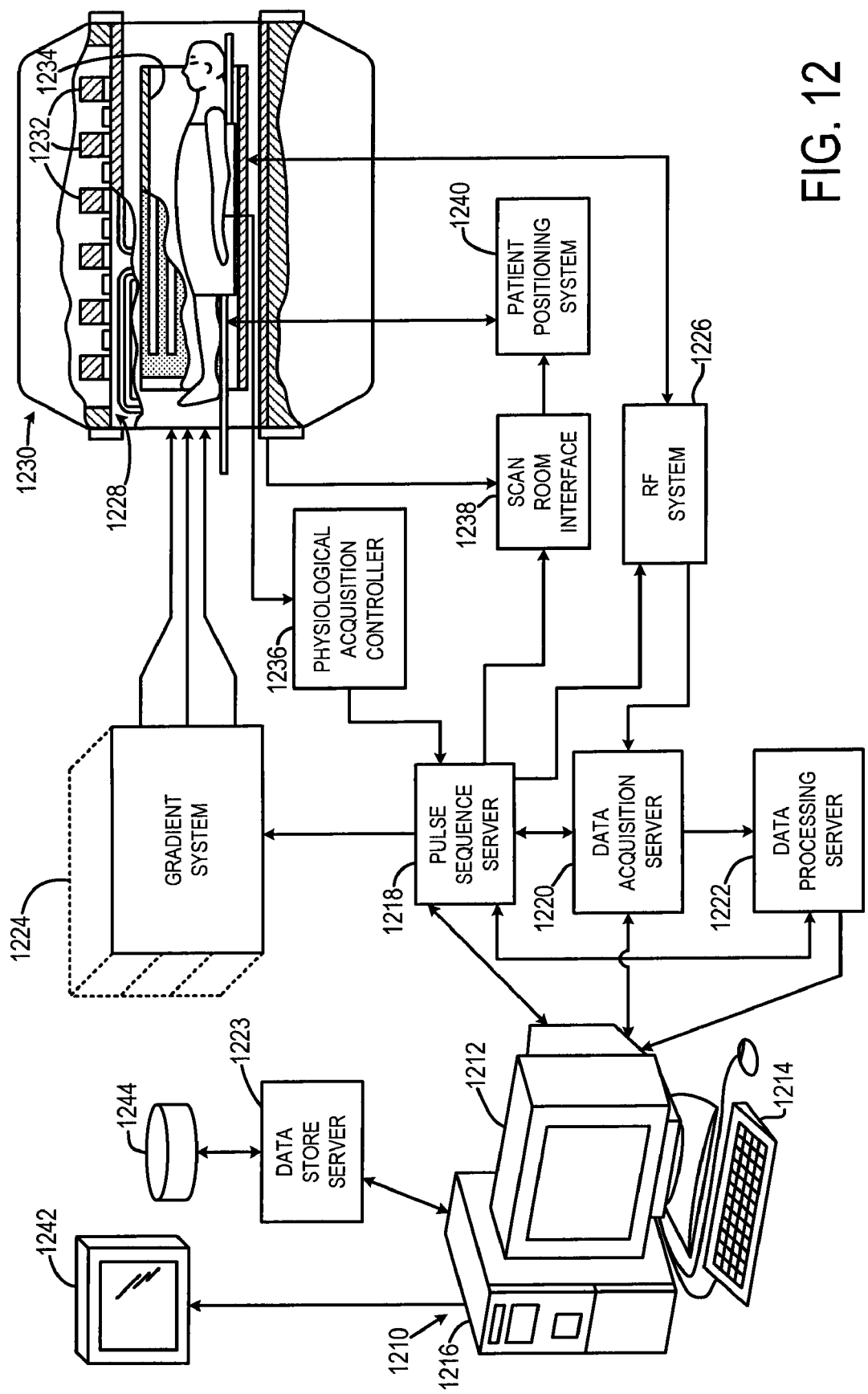
FIG. 12 is a block diagram of a magnetic resonance imaging (MRI) system used to practice the present invention.

The present invention is also particularly applicable to other medical imaging modalities. One such imaging modality is magnetic resonance imaging (MRI). Referring particularly to FIG. 12, the method of the present invention can be employed in an MRI system. The MRI system includes a workstation 1210 having a display 1212 and a keyboard 1214. The workstation 1210 includes a processor 1216 that is a commercially available programmable machine running a commercially available operating system. The workstation 1210 provides the operator interface that enables scan prescriptions to be entered into the MRI system. The workstation 1210 is coupled to four servers: a pulse sequence server 1218; a data acquisition server 1220; a data processing server 1222, and a data store server 1223. The workstation 1210 and each server 1218, 1220, 1222 and 1223 are connected to communicate with each other.

The pulse sequence server 1218 functions in response to instructions downloaded from the workstation 1210 to operate a gradient system 1224 and an RF system 1226. Gradient waveforms necessary to perform the prescribed scan are produced and applied to the gradient system 1224 that excites gradient coils in an assembly 1228 to produce the magnetic field gradients $G_x$, $G_y$ and $G_z$ used for position encoding MR signals. The gradient coil assembly 1228 forms part of a magnet assembly 1230 that includes a polarizing magnet 1232 and a whole-body RF coil 1234.

RF excitation waveforms are applied to the RF coil 1234 by the RF system 1226 to perform the prescribed magnetic resonance pulse sequence. Responsive MR signals detected by the RF coil 1234 or a separate local coil (not shown in FIG. 12) are received by the RF system 1226, amplified, demodulated, filtered and digitized under direction of commands produced by the pulse sequence server 1218. The RF system 1226 includes an RF transmitter for producing a wide variety of RF pulses used in MR pulse sequences. The RF transmitter is responsive to the scan prescription and direction from the pulse sequence server 1218 to produce RF pulses of the desired frequency, phase and pulse amplitude waveform. The generated RF pulses may be applied to the whole body RF coil 1234 or to one or more local coils or coil arrays (not shown in FIG. 12).

The RF system 1226 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2},$$

and the phase of the received MR signal may also be determined:

$$\phi = \tan^{-1}\left(\frac{Q}{I}\right).$$

The pulse sequence server 1218 also optionally receives patient data from a physiological acquisition controller 1236. The controller 1236 receives signals from a number of different sensors connected to the patient, such as ECG signals from electrodes or respiratory signals from a bellows. Such signals are typically used by the pulse sequence server 1218 to synchronize, or "gate", the performance of the scan with the subject's respiration or heart beat.

The pulse sequence server 1218 also connects to a scan room interface circuit 1238 that receives signals from various sensors associated with the condition of the patient and the magnet system. It is also through the scan room interface circuit 1238 that a patient positioning system 1240 receives commands to move the patient to desired positions during the scan.

The digitized MR signal samples produced by the RF system 1226 are received by the data acquisition server 1220. The data acquisition server 1220 operates in response to instructions downloaded from the workstation 1210 to receive the real-time MR data and provide buffer storage such that no data is lost by data overrun. In some scans the data acquisition server 1220 does little more than pass the acquired MR data to the data processor server 1222. However, in scans that require information derived from acquired MR data to control the further performance of the scan, the data acquisition server 1220 is programmed to produce such information and convey it to the pulse sequence server 1218. For example, during prescans MR data is acquired and used to calibrate the pulse sequence performed by the pulse sequence server 1218. Also, navigator signals may be acquired during a scan and used to adjust RF or gradient system operating parameters or to control the view order in which k-space is sampled. And, the data acquisition server 1220 may be employed to process MR signals used to detect the arrival of contrast agent in an MRA scan. In all these examples the data acquisition server 1220 acquires MR data and processes it in real-time to produce information that is used to control the scan.

The data processing server 1222 receives MR data from the data acquisition server 1220 and processes it in accordance with instructions downloaded from the workstation 1210. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 1222 are conveyed back to the workstation 1210 where they are stored. Real-time images are stored in a data base memory cache (not shown) from which they may be output to operator display 1212 or a display 1242 that is located near the magnet assembly 1230 for use by attending physicians. Batch mode images or selected real time images are stored in a host database on disc storage 1244. When such images have been reconstructed and transferred to storage, the data processing server 1222 notifies the data store server 1223 on the workstation 1210. The workstation 1210 may be used by an operator to archive the images, produce films, or send the images via a network to other facilities.

Like the CT system, the MRI system has many different clinical applications in which either 2D or 3D sets of projection views are acquired and used to reconstruct one or more images of the patient. Whereas the projection views acquired by the CT system include Radon space samples, the projection views acquired by the MRI system include k-space (or Fourier space) samples. Image reconstruction using data acquired with an MRI system necessarily requires transformation from k-space to real space, or as an intermediate step, into Radon space.

Exemplary Magnetic Resonance Imaging Pulse Sequence

Figure 13:
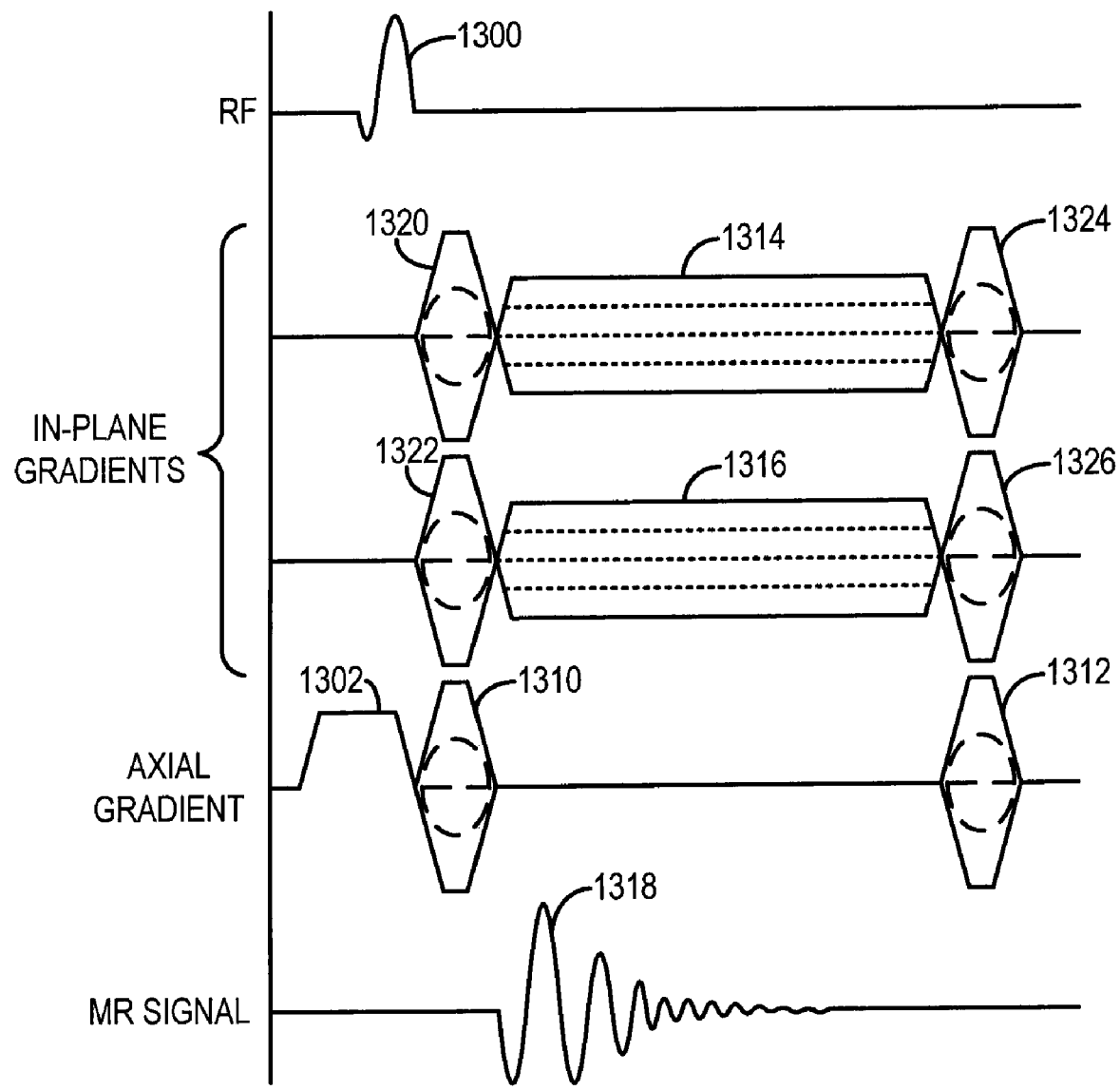
FIG. 13 is a pulse sequence used in the MRI system of FIG. 12 to practice one embodiment of the invention.
Figure 14:
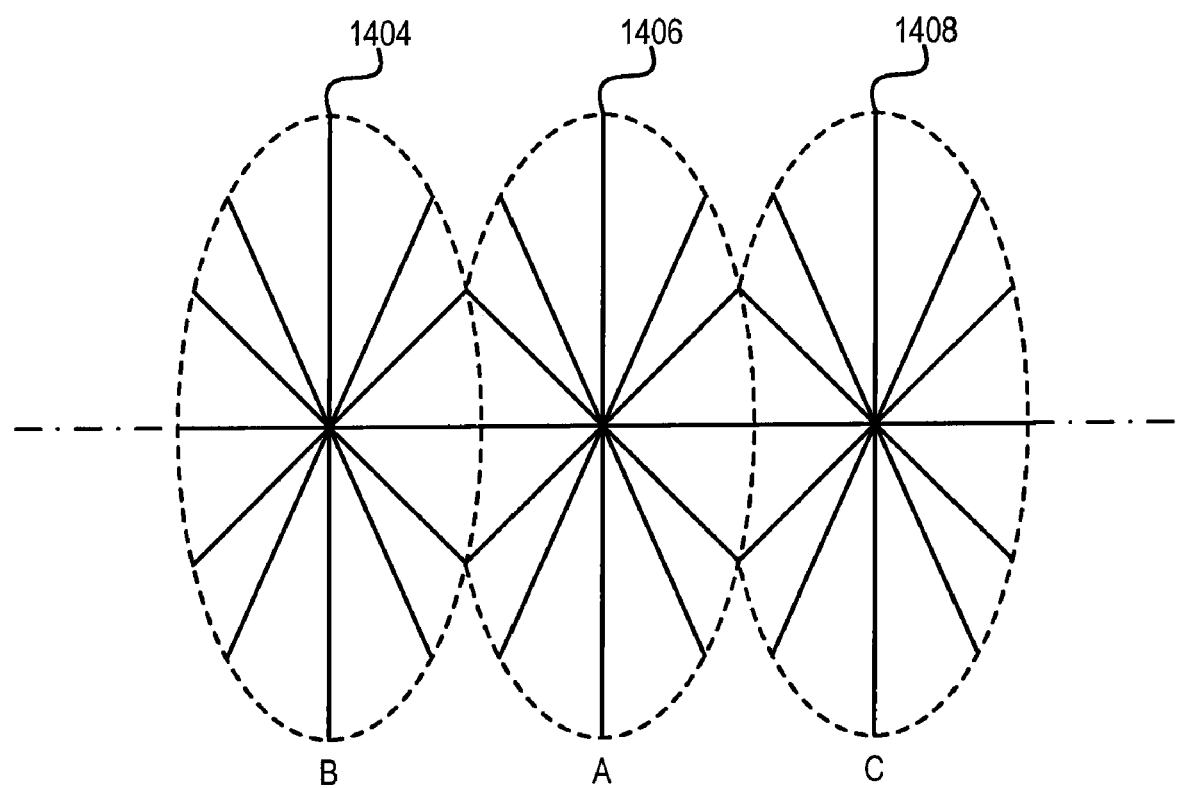
FIG. 14 is a pictorial representation of the k-space data sampled using the pulse sequence of FIG. 13.

To practice the present invention using an MR imaging system, such as the one described above with reference to FIG. 12, undersampled image data is acquired using a projection reconstruction, or radial, pulse sequence such as that shown in FIG. 13. This is a fast gradient-recalled echo pulse sequence in which a selective, asymmetrically truncated sinc RF excitation pulse 1300 is produced in the presence of a slice-select gradient 1302. This pulse sequence may be used to acquire a single 2D slice by sampling in a single k-space circular plane, or it may be used to sample a plurality of circular k-space planes as shown at 1404, 1406, and 1408 in FIG. 14. When multiple 2D slices are acquired the gradient 1302 is a slab select gradient followed by a phase encoding gradient lobe 1310 and a rewinder gradient lobe 1312 of opposite polarity. This axial, phase encoding gradient 1310 is stepped through values during the scan to sample from each of the 2D k-space planes 1404, 1406, and 1408.

Two in-plane readout gradients 1314 and 1316 are played out during the acquisition of an NMR echo signal 1318 to sample k-space in a 2D plane 1404, 1406, or 1408 along a radial trajectory. These in-plane gradients 1314 and 1316 are perpendicular to the axial gradient and they are perpendicular to each other. During a scan they are stepped through a series of values to rotate the view angle of the radial sampling trajectory as will be described in more detail below. Each of the in-plane readout gradients is preceded by a prephasing gradient lobe 1320 and 1322 and followed by a rewinder gradient lobe 1324 and 1326.

It should be apparent to those skilled in the art that sampling trajectories other than the preferred straight line trajectory extending from one point on the k-space peripheral boundary, through the center of k-space to an opposite point on the k-space peripheral boundary may also be used. As mentioned above, one variation is to acquire a partial NMR echo signal 1303 that samples along a trajectory that does not extend across the entire extent of the sampled k-space volume. Another variation which is equivalent to the straight line projection reconstruction pulse sequence is to sample along a curved path rather than a straight line. Such pulse sequences are described, for example, by F. E. Boada, et al., in "Fast Three Dimensional Sodium Imaging", *Magnetic Resonance in Medicine*, 1997; 37:706-715, by K. V. Koladia, et al., in "Rapid 3D PC-MRA Using Spiral Projection Imaging", *Proc. Intl. Soc. Magn. Reson. Med.* 13 (2005), and by J. G. Pipe and K. V. Koladia in "Spiral Projection Imaging: a new fast 3D trajectory", *Proc. Intl. Soc. Mag. Reson. Med.* 13 (2005). It should also be apparent that the present invention may be employed with 3D as well as 2D versions of these sampling methods and use of the term "pixel" herein is intended to refer to a location in either a 2D or a 3D image. Moreover, the present invention is applicable to reconstructing an image from undersampled image data acquired by employing any number of pulse sequences and sampling patterns, as will be appreciated by those skilled in the art.

The MRI system described above can be used in a wide variety of clinical applications to acquire either 2D or 3D sets of projection views that may be used to reconstruct one or more images. The image reconstruction method of the present invention is particularly useful in scans where one or more image frames are reconstructed using less than all the acquired projection views.

Magnetic Resonance Image Reconstruction

Figure 15:
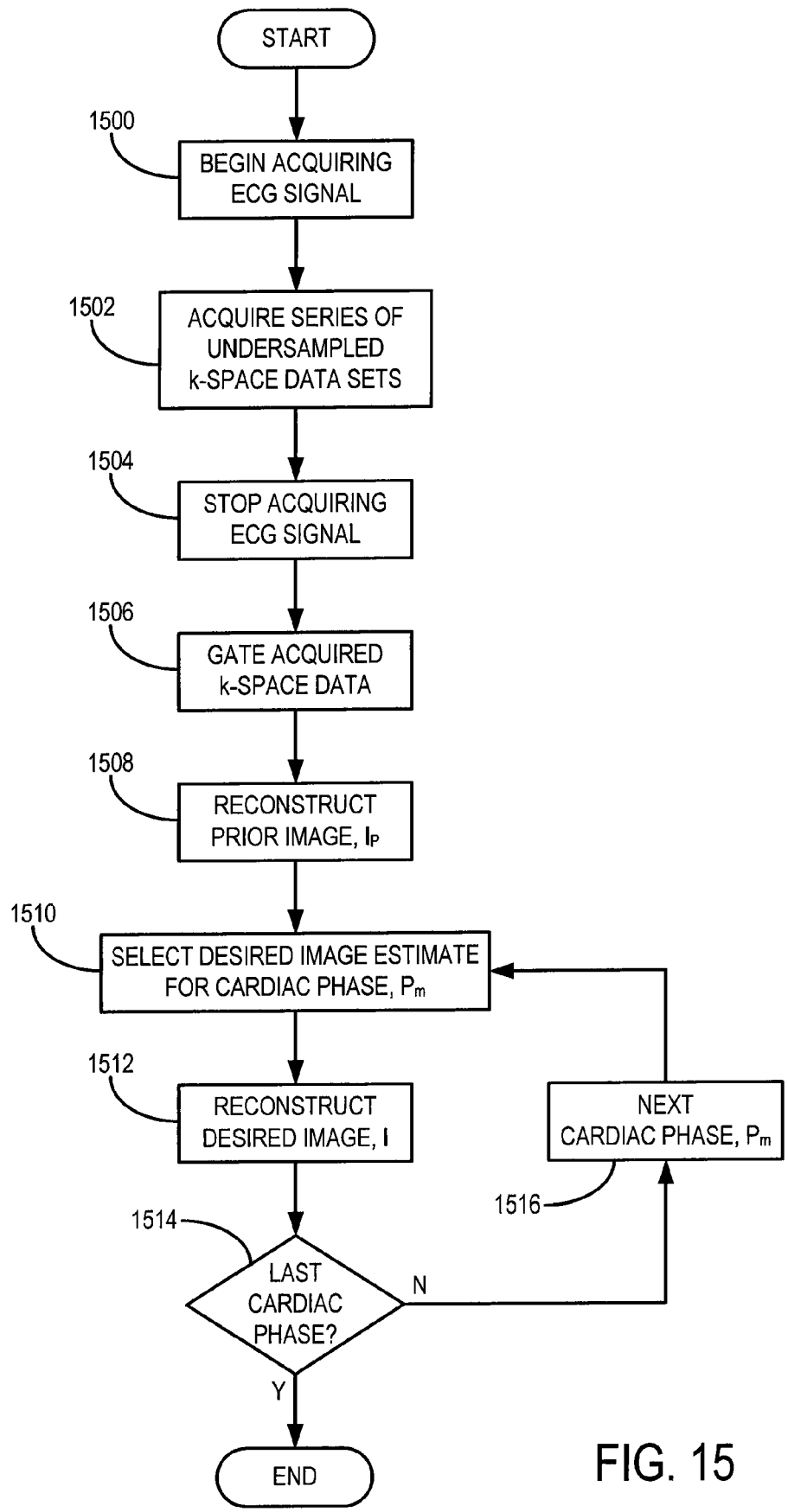
FIG. 15 is a flowchart of yet another embodiment of the invention used in the MRI system of FIG. 10 with the pulse sequence of FIG. 11.
Figure 16:
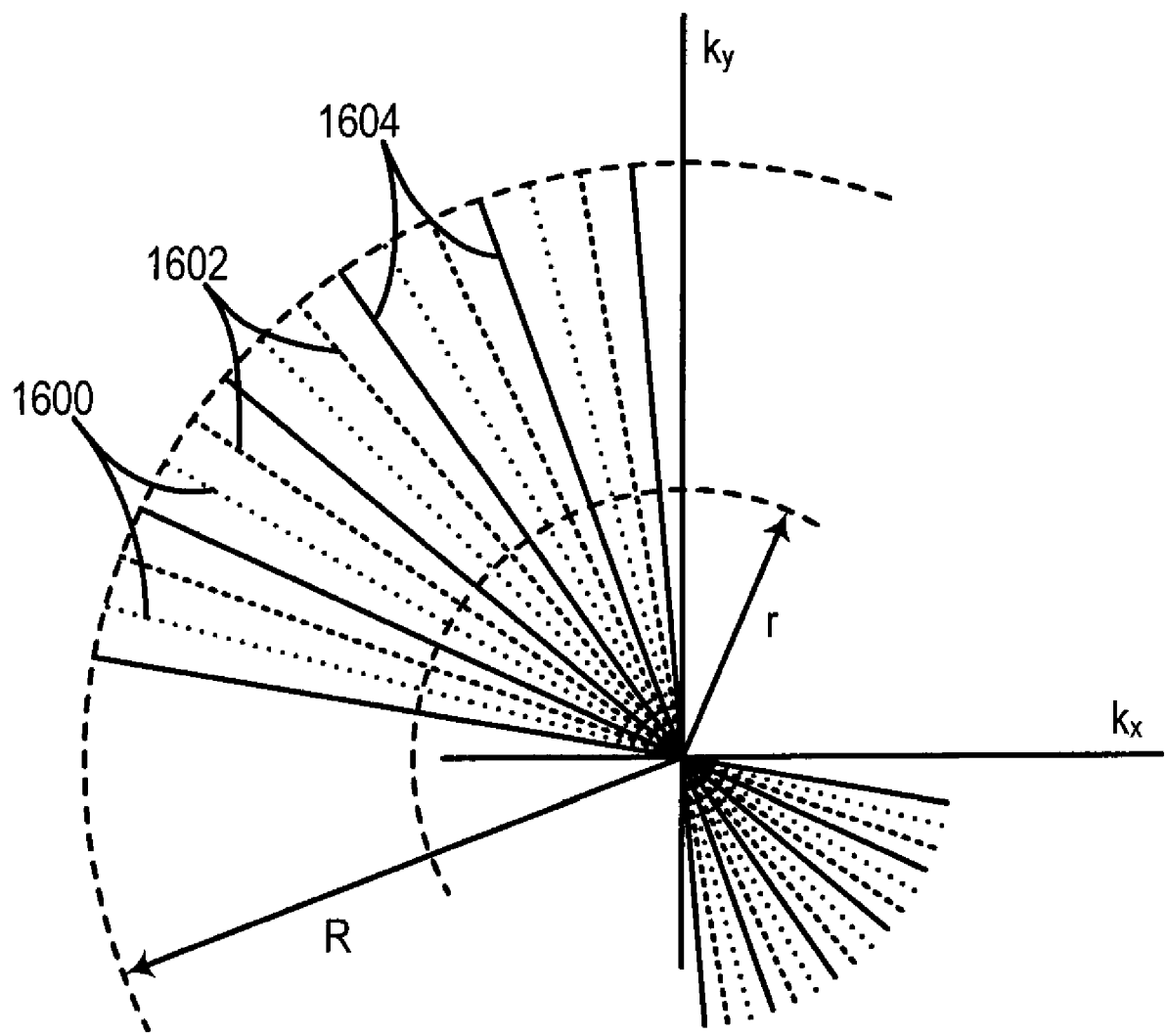
FIG. 16 is a graphic representation of interleaved projection views.

Referring particularly to FIG. 15, when practiced in an MR imaging system, such as the one described above in FIG. 12, the method of the present invention starts by acquiring an electrocardiogram (ECG) signal from the subject, as indicated at step 1500. This ECG signal is used to retrospectively gate the acquired image data into M different cardiac phases, $P_M$. Next, image data in the form of a series of undersampled k-space data sets is acquired, as indicated at step 1502. As described above, the undersampled image data is acquired by directing the MR imaging system to perform a pulse sequence, such as the one shown in FIG. 13, that samples k-space with a series of undersampled radial interleaves. An exemplary k-space sampling pattern is shown, for example, in FIG. 16. As noted above, the k-space data acquired for each desired image frame is highly undersampled in order to increase the temporal resolution of the study. Moreover, the projection views acquired for each undersampled image frame are interleaved with the projection views acquired for the other image frames. For example, the projections acquired with the k-space sampling indicated by dotted lines 1600, the k-space sampling indicated by dashed lines 1602, and the k-space sampling indicated by solid lines 1604 are all interleaved with each other such that none sample the same locations in k-space. Each of these sampling patterns correspond to an individual image frame. When the data acquisition is completed, the acquisition of the ECG signal is stopped, as indicated at step 1504. The acquired image data is subsequently gated, retrospectively, into the M different cardiac phases, $P_m$, as described above in detail and indicated at step 1506. This retrospective gating produces a "cardiac phase image data set" for each of the M different desired cardiac phases. Therefore, each cardiac phase image data set includes a plurality of projection views acquired during the gating window, $W_m$, corresponding to a given cardiac phase, $P_m$. In the alternative, the original image data acquisition can be prospectively gated such that image data is only acquired at specific time points during the ECG signal. Following this data acquisition scheme, all of the image data acquired during a selected cardiac phase is similarly combined into a cardiac phase image data set.

Since each cardiac phase image data set is highly undersampled, an attempt to reconstruct images using standard image reconstruction algorithms, such as the regridding method described above, will result in severe streaking artifacts. Therefore, the method of the present invention proceeds by reconstructing a prior image, $I_P$, as indicated in step 1508.

The prior image, $I_P$, is produced from an image data set that combines acquired data from successive k-space interleaves. Moreover, the prior image is produced by accumulating or averaging a plurality of different k-space interleaves. Such a prior image will inherently lose the dynamic information associated with the beating heart, since the image data was acquired over a plurality of different cardiac phases; however, this dynamic information is recovered when reconstructing the desired images of each cardiac phase. In the alternative, however, the prior image can be reconstructed using other image reconstruction methods such as, for example, HYPR, HYPR-LR, and I-HYPR. By employing the HYPR-LR method, for example, a further increase in the signal-to-noise ratio (SNR) is possible in the desired image.

Proceeding with the image reconstruction method, an estimate of the desired image for a given cardiac phase, $P_m$, is produced at step 1510. For example, this estimate can be an image reconstructed from the appropriate cardiac phase image data set using a regridding or other convention MR image reconstruction method. In the alternative, however, the prior image, $I_P$, can be selected as the estimate image. A desired image, I, of the selected cardiac phase, $P_m$, is subsequently reconstructed in accordance with the method of the present invention described above with reference to FIGS. 3, 4, and 5, as indicated in step 1512. Since the prior image, $I_P$, is not a high quality image, the regularization parameter, $\alpha$, is selected to mitigate the effects of the poor quality of the prior image, $I_P$. For example, a value of $\alpha \approx 0.3$-$0.7$ is employed. A desired image, I, is reconstructed for each cardiac phase, $P_m$, in this manner until an image for all of the desired cardiac phases has been reconstructed, as decided at process block 1514. If all of the desired images have not been reconstructed, the method selects the next cardiac phase, $P_m$, at step 1516 and proceeds with the image reconstruction method.

It should be appreciated by those skilled in the art that for the above described magnetic resonance image reconstruction method, many equivalents, alternatives, variations, and modifications, aside from those expressly stated, are possible and within the scope of the invention. For example, the subject's respiration can be monitored with a respiration monitoring device, such as a respiratory belt, and image data retrospectively gated based on the measured respiratory information. In this manner, motion, such as internal organ motion, can be compensated for when reconstructing images. Similarly, the subject's motion can be monitored by acquiring navigator signals during the data acquisition process. Using the information in the navigator signals, the image data can subsequently be retrospectively gated as described above. Moreover, by monitoring the subject's respiration, imaging of the lungs, such as hyperpolarized helium-3 MR imaging, can be performed with increased temporal resolution. In general, the method of the present invention can utilize any signal indicative of subject motion to gate, or divide, acquired image data into a plurality of "motion phase image data sets".

Positron Emission Tomography System

Figure 17:
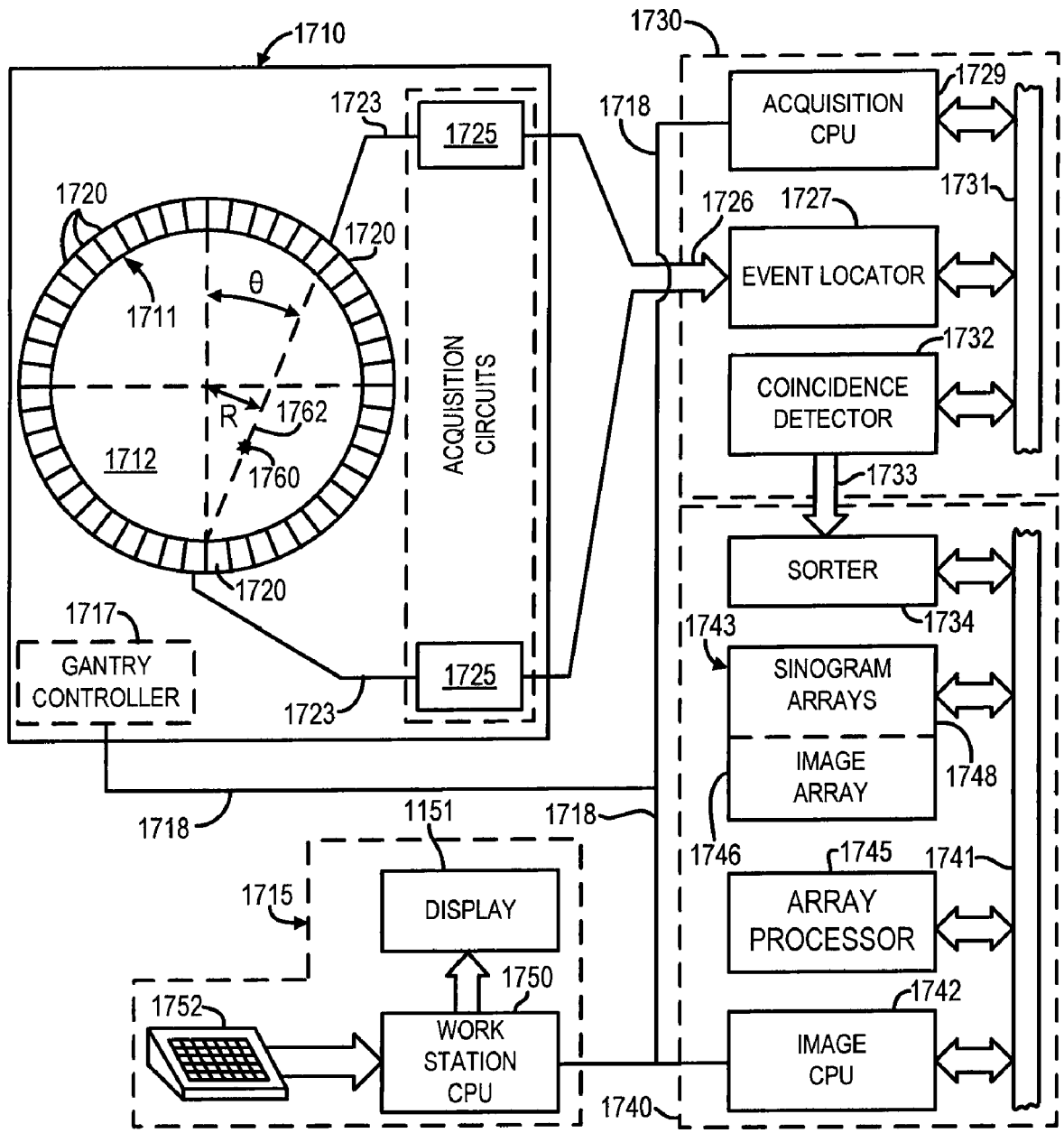
FIG. 17 is a block diagram of a positron emission tomography (PET) imaging system.

Referring particularly to FIG. 17, the PET scanner system includes a gantry 1710 which supports a detector ring assembly 1711 about a central opening, or bore 1712. A gantry controller 1717 is mounted within the gantry 1710 and is responsive to commands received from an operator work station 1715 through a second serial communication link 1718 to operate the gantry.

The detector ring 1711 is comprised of detector blocks 1720. Each block 1720 includes a set of scintillator crystal photomultiplier tubes. A set of acquisition circuits 1725 are mounted within the gantry 1710 to receive the signals from each of the modules 1720 in the detector ring 1711. The acquisition circuits 1725 determine the event coordinates within each block of scintillator crystals and these coordinates (x,z), along with the sum of the crystal block signals are digitized and sent through a cable 1726 to an event locater circuit 1727 housed in a separate cabinet 1728. Each acquisition circuit 1725 also produces an event detection pulse (EDP) which indicates the exact moment the scintillation event took place.

The event locator circuits 1727 form part of a data acquisition processor 1730 which periodically samples the signals produced by the acquisition circuits 1725. The processor 1730 has a backplane bus structure 1731 and an acquisition CPU 1729 which controls communications on this bus 1731 and links the processor 1730 to the local area network 1718. The event locator 1727 is comprised of a set of separate circuit boards which each connect to the cable 1726 and receive signals from corresponding acquisition circuits 1725 in the gantry 1710. The event locator 1727 synchronizes the event with the operation of the processor 1730 by detecting the event pulse (EDP) produced by an acquisition circuit 1725, and converting it into an 8-bit time marker which indicates when within the current sample period the scintillation event took place. Also, this circuit 1727 discards any detected events if the total energy of the scintillation is outside the range of 511 keV±20%. During each sample period, the information regarding each valid event is assembled into a set of digital numbers that indicate precisely when the event took place and the position of the scintillator crystal which detected the event. This event data packet is conveyed to a coincidence detector 1732 which is also part of the data acquisition processor 1730.

The coincidence detector 1732 accepts the event data packets from the event locators 1727 and determines if any two of them are in coincidence. Events which cannot be paired are discarded, but coincident event pairs are located and recorded as a coincidence data packet that is conveyed through a serial link 1733 to a sorter 1734. Each coincidence data packet includes a pair of digital numbers which precisely identify the addresses of the two scintillator crystals that detected the event. From these, the location and angle of the ray path that produced the coincidence event can be determined.

The sorter 1734 is a circuit which forms part of an image reconstruction processor 1740. The image reconstruction processor 1740 is formed about a backplane bus 1741. An image CPU 1742 controls the backplane bus 1741 and it links the processor 1740 to the local area network 418. A memory module 1743 also connects to the backplane 1741 and it stores the data used to reconstruct images as will be described in more detail below. An array processor 1745 also connects to the backplane 1741 and it operates under the direction of the image CPU 1742 to perform the image reconstruction using the data in memory module 1743. The resulting image array 1746 is stored in memory module 1743 and is output by the image CPU 1742 to the operator work station 1715.

The function of the sorter 1734 is to receive the coincidence data packets and generate from them memory addresses for the efficient storage of the coincidence data. The set of all coincidence event rays that point in the same direction (θ) and pass through the scanner's field of view is a complete projection, or "view". The distance (R) between a particular ray path in a projection view and the center of the field of view locates that ray within the view. As shown in FIG. 17, for example, an event 1760 occurs along a projection ray 1762 which is located in a view at the projection angle θ and the distance R. The sorter 1734 counts all of the events that occur on this projection ray (R,θ) during the scan by sorting out the coincidence data packets that indicate an event at the two scintillator crystals lying on this projection ray. During an emission scan, the coincidence counts are organized in memory 1743 as a set of two-dimensional arrays, one for each axial image, and each having as one of its dimensions the projection angle θ and the other dimension the distance R. This θ by R map of the measured coincidence events is called a histogram, or more commonly the sinogram array 1748.

Coincidence events occur at random and the sorter 1734 quickly determines the θ and R values from the two scintillator crystal addresses in each coincidence data packet and increments the count of the corresponding sinogram array element. At the completion of the emission scan, the sinogram array 1748 stores the total number of annihilation events which occurred along each ray. The number of such annihilation events indicates the number of positron electron annihilation events that occurred along the ray (R,θ) during the emission scan and within a few minutes hundreds of thousands of events are typically recorded. These numbers are used to reconstruct a tomographic image.

It can be appreciated that the quality of a PET image will depend to a great extent on the number of scintillation events that are allowed to accumulate in the sinogram 1748. The longer the scan continues, the larger the number of detected scintillation events and the higher the quality of the reconstructed image.

Positron Emission Tomography Image Reconstruction

Figure 18:
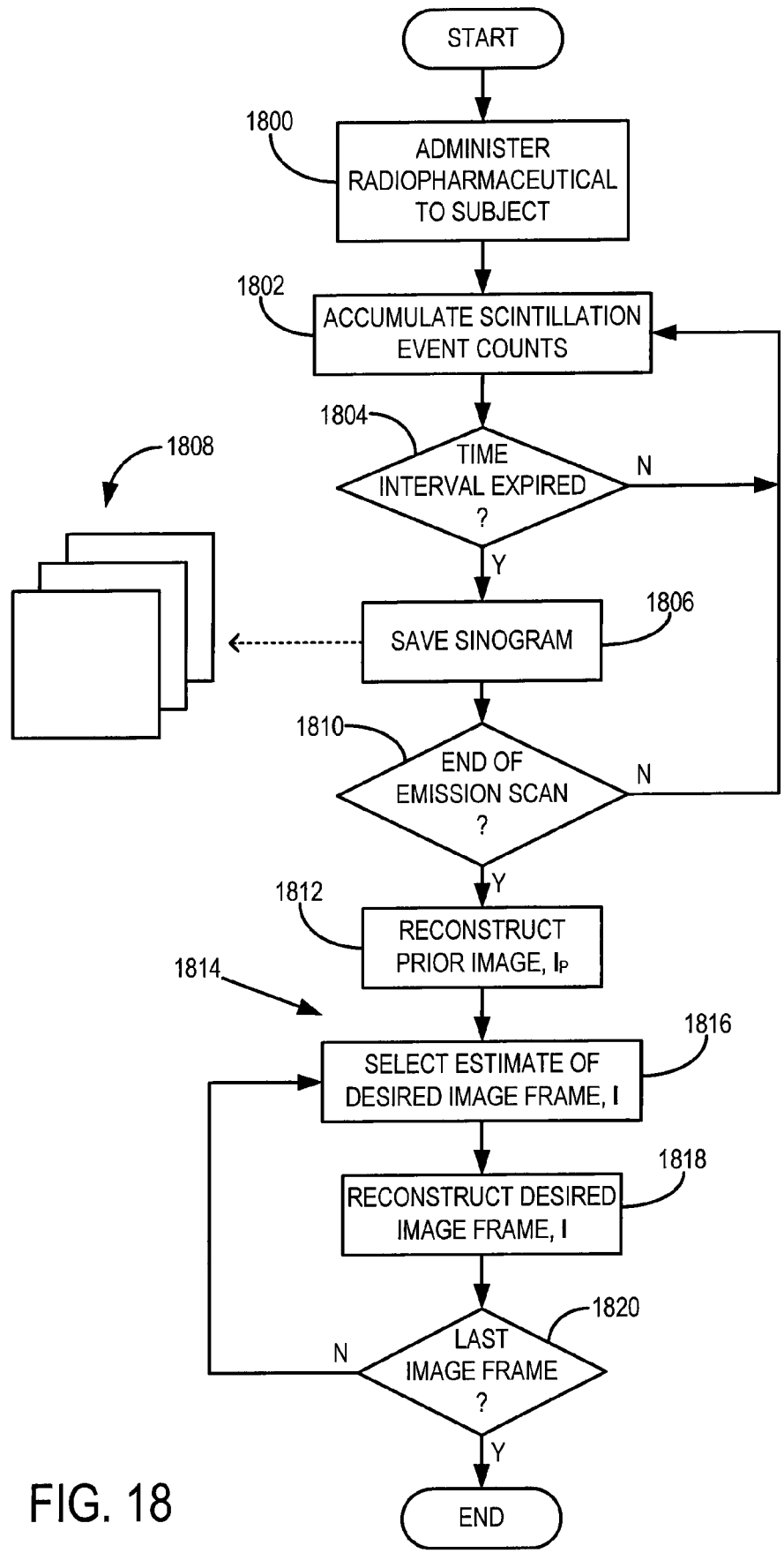
FIG. 18 is a flowchart of yet another embodiment of the present invention using the PET imaging system of FIG. 17.

Referring particularly to FIG. 18, the present invention may be employed by the PET scanner to perform a time-resolved emission scan. The emission scan begins as indicated at process block 1800 by injecting a radionuclide into the subject of the examination. The radionuclides most often employed in diagnostic imaging are fluorine-18 ($^{18}F$), carbon-11 ($^{11}C$), nitrogen-13 ($^{13}N$), and oxygen-15 ($^{15}O$). These are employed as radioactive tracers called "radiopharmaceuticals" by incorporating them into substances, such as glucose or carbon dioxide. The radiopharmaceuticals are injected in the patient and become involved in such processes as glucose metabolism, fatty acid metabolism and protein synthesis.

The subject is placed in the bore 1712 of the PET scanner and scintillation events are detected and counted as indicated at process block 1802. As described above, the scintillation events are detected, sorted and stored in a sinogram 1748 as counts for each ray R in the projection views θ. Events are counted and accumulated for a relatively short time interval as determined at decision block 1804. As indicated at process block 1806, when the time interval expires the accumulated scintillation event counts are saved as a time interval sinogram 1808.

The emission scan continues and the accumulated sinogram count is saved after each time interval until the end of the scan is detected at decision block 1810. End of scan may be a preset time or a preset number of time intervals. In either case, a plurality of time interval sinograms 1808 will be produced during the emission scan and the last sinogram 1808 will store the total count for the entire emission scan. Each time interval sinogram 1808 is analogous to an image data set acquired with the MR and CT imaging systems described above.

The image reconstruction phase of the scan now begins, and during this phase an image frame indicative of the uptake of radiopharmaceutical at the end of each time interval is reconstructed. First, as indicated at process block 1812, a prior image, $I_P$, is reconstructed. This is a conventional back-projection reconstruction using the last sinogram 1808 saved during the emission scan. This contains the accumulated scintillation events for the entire emission scan and the image quality will be the best possible. In the alternative, a previously acquired x-ray computed tomography image of the subject can be utilized as the prior image, $I_P$. If this computed tomography image is acquired with a combined PET/CT imaging system, then registration of the prior image, $I_P$, with the acquired time interval sinograms 1808 is likely not required. However, if the computed tomography image is acquired with a different imaging system, image registration is required.

A loop is then entered at 1814 in which time resolved image frames, I, are reconstructed using the prior image, $I_P$. More specifically, as indicated at process block 1816 an estimate of desired image frame is first selected. This estimate image may be produced by performing conventional back-projection reconstruction on the desired time interval sinogram 1808, or, in the alternative, the estimate image can be selected as the prior image, $I_P$. The image frame reconstruction process 1818 is subsequently performed in accordance with the method of the present invention described above with respect to FIGS. 3, 4, and 5. This is repeated until image frames corresponding to each time interval sinogram 1808 are produced as determined at decision block 1820. As a result, a series of image frames are produced which indicate the uptake of the radiopharmaceutical at each time interval during the emission scan. By using the higher quality prior image in the reconstruction, the image quality of each image frame is substantially improved over conventional images reconstructed using sinograms having low annihilation event counts.

It should be appreciated by those skilled in the art that the same above described image reconstruction strategy can be utilized for reconstructing images acquired with single photon emission computed tomography (SPECT) systems. As with PET scanners, SPECT systems accumulate counts of detected photons emitted from the subject along different ray paths. During a scan a gamma camera is moved slowly to accumulate counts at different view angles. Using the present invention a series of image frames may be acquired by moving the gamma camera more quickly and repeatedly through the same series of view angles. A lower count is accumulated at each view angle so as not to increase total scan time, but the SNR of each reconstructed image frame is maintained using a sparsifying image that is formed by adding all the counts together for each view angle.

The present invention has been described in terms of one or more preferred embodiments, and it should be appreciated that many equivalents, alternatives, variations, and modifications, aside from those expressly stated, are possible and within the scope of the invention. For example, the method of the present invention can be practiced in any imaging system in order to enhance the temporal resolution of image data acquired therewith.

The invention claimed is:

1. A method for reconstructing an image of a subject with an imaging system, the steps comprising:
   a) acquiring, with the imaging system, a time series of image data of the subject;
   b) selecting an estimate image of the subject;
   c) reconstructing a prior image of the subject from the time series of image data acquired in step a);
   d) producing a sparsified image of the subject using the prior image and the estimate image; and
   e) reconstructing a desired image of the subject using the sparsified image, the estimate image, and the acquired time series of image data.

2. The method as recited in claim 1 in which steps b)-e) are repeated to produce a time series of desired images.

3. The method as recited in claim 2 in which the time series of image data is acquired with a first temporal resolution and the time series of desired images is indicative of a second temporal resolution that is higher than the first temporal resolution.

4. The method as recited in claim 1 further comprising:
   f) acquiring a signal indicative of subject motion; and
   g) producing a motion phase image data set from the acquired time series of image data.

5. The method as recited in claim 4 in which step g) includes:
   selecting a gating window indicative of a time period in the acquired signal indicative of subject motion; and
   selecting, from the acquired time series of image data, image data acquired during the gating window.

6. The method as recited in claim 5 in which step g) further includes:
   dividing the selected gating window into a plurality of time windows; and
   dividing the motion phase image data set into a corresponding plurality of motion subphase image data sets using the plurality of time windows.

7. The method as recited in claim 4 in which step b) includes reconstructing the estimate image from the motion phase image data set.

8. The method as recited in claim 4 in which the subject motion is physiological motion of the heart, the signal indicative of the subject motion is an electrocardiogram (ECG) signal, and the motion phase image data set is a cardiac phase image data set.

9. The method as recited in claim 1 in which step d) includes subtracting the prior image from the estimate image.

10. The method as recited in claim 1 in which step e) includes:
    e)i) producing an objective function using the sparsified image, the estimate image, and the acquired time series of image data; and
    e)ii) reconstructing the desired image by iteratively minimizing the objective function.

11. The method as recited in claim 10 in which step e)i) includes:

producing at least a first and second objective function term, wherein the at least first objective function term is produced by applying a sparsifying transform to the sparsified image and the at least second objective function term is produced by applying a sparsifying transform to the estimate image; and adding the at least first and second objective function terms.

12. The method as recited in claim 11 in which step e)i) further includes calculating a norm of the at least first and second objective function terms and weighting the calculated norms using a regularization parameter.

13. The method as recited in claim 10 in which the objective function has at least one of the following forms:

$$\alpha\|\Psi_1(I-I_P)\|_p+(1-\alpha)\|\Psi_2 I\|_p;$$

$$\alpha\|\Psi_1(I-I_P)\|_p+(1-\alpha)\|\Psi_2 I\|_p+\lambda\|X\|_2^2; \text{ and}$$

$$\alpha\|\Psi_1(I-I_P)\|_p+(1-\alpha)\|\Psi_2 I\|_p+\lambda(X^T DX);$$

wherein:
- $\alpha$ is a regularization parameter;
- $\Psi_1$ is a first sparsifying transform;
- $\Psi_2$ is a second sparsifying transform;
- $I$ is the estimate image;
- $I_P$ is the prior image;
- $\|\ldots\|_p$ is an $L_p$-norm;
- $\lambda$ is a Lagrange multiplier;
- $X$ is a difference matrix indicative of the difference between the acquired time series of image data and a forward projection of the estimate image; and
- $D$ is a system noise matrix.

14. The method as recited in claim 1 in which the imaging system is at least one of a magnetic resonance imaging (MRI) system, an x-ray computed tomography (CT) imaging system, a C-arm x-ray imaging system, a positron emission tomography (PET) imaging system, and a single photon emission computed tomography (SPECT) imaging system.

15. A method for reconstructing a time series of images of a subject with an imaging system, the steps comprising:

a) acquiring, with the imaging system at a first temporal resolution, a time series of image data of the subject;
b) selecting an estimate image of the subject;
c) reconstructing a prior image of the subject from the time series of image data acquired in step a);
d) producing a sparsified image of the subject using the prior image and the estimate image; and
e) reconstructing a time series of desired images of the subject using the sparsified image, the estimate image, and the acquired time series of image data, wherein the time series of desired images of the subject is indicative of a second temporal resolution that is higher than the first temporal resolution.

16. The method as recited in claim 15 further comprising:

f) acquiring a signal indicative of subject motion; and
g) producing a motion phase image data set from the acquired time series of image data.

17. The method as recited in claim 16 in which step g) includes:

selecting a gating window indicative of a time period in the acquired signal indicative of subject motion; and
selecting, from the acquired time series of image data, image data acquired during the gating window.

18. The method as recited in claim 17 in which step g) further includes:

dividing the selected gating window into a plurality of time windows; and
dividing the motion phase image data set into a corresponding plurality of motion subphase image data sets using the plurality of time windows.

19. The method as recited in claim 16 in which step b) includes reconstructing the estimate image from the motion phase image data set.

20. The method as recited in claim 16 in which the subject motion is physiological motion of the heart, the signal indicative of the subject motion is an electrocardiogram (ECG) signal, and the motion phase image data set is a cardiac phase image data set.

* * * * *